(12) United States Patent
Gianotti et al.

(10) Patent No.: US 10,632,005 B2
(45) Date of Patent: Apr. 28, 2020

(54) CATHETER SYSTEM FOR TREATING VASCULAR AND NON-VASCULAR DISEASES

(71) Applicant: CTI Vascular AG, Neuhausen (CH)

(72) Inventors: Marc Gianotti, Wiesendangen (CH); Ulf Fritz, Tengen (DE)

(73) Assignee: CTI VASCULAR AG, Neuhausen (DE)

( * ) Notice: Subject to any disclaimer, the term of this patent is extended or adjusted under 35 U.S.C. 154(b) by 0 days.

(21) Appl. No.: 16/334,111

(22) PCT Filed: Dec. 14, 2016

(86) PCT No.: PCT/EP2016/080988
§ 371 (c)(1),
(2) Date: Mar. 18, 2019

(87) PCT Pub. No.: WO2018/050262
PCT Pub. Date: Mar. 22, 2018

(65) Prior Publication Data
US 2019/0254846 A1    Aug. 22, 2019

Related U.S. Application Data

(60) Provisional application No. 62/396,787, filed on Sep. 19, 2016.

(51) Int. Cl.
*A61F 2/90* (2013.01)
*A61F 2/01* (2006.01)
(Continued)

(52) U.S. Cl.
CPC .......... *A61F 2/90* (2013.01); *A61B 17/12118* (2013.01); *A61F 2/013* (2013.01);
(Continued)

(58) Field of Classification Search
CPC .... A61F 2/01; A61F 2/013; A61F 2/90; A61F 2/95; A61F 2002/011; A61F 2002/016;
(Continued)

(56) References Cited

U.S. PATENT DOCUMENTS

| 5,817,101 A * | 10/1998 | Fiedler ...................... A61F 2/95 |
| | | 623/1.11 |
| 2002/0045929 A1* | 4/2002 | Diaz ......................... A61F 2/95 |
| | | 623/1.11 |

(Continued)

FOREIGN PATENT DOCUMENTS

| WO | WO 98/38920 A1 | 7/2005 |
| WO | WO 2003/125764 A1 | 7/2005 |
| WO | WO 2013/109756 A2 | 7/2013 |

*Primary Examiner* — Darwin P Erezo
*Assistant Examiner* — Christian D Knauss
(74) *Attorney, Agent, or Firm* — Smith Patent, LLC; Chalin A. Smith

(57) ABSTRACT

The present invention relates to a catheter system and methods of using such catheter system for the treatment of vascular and non-vascular pathologies. More specifically, the present invention is directed towards a catheter system for the actuation of a temporarily implantable member elastically deformable by hydraulic means.

16 Claims, 17 Drawing Sheets

(51) Int. Cl.
    *A61F 2/95*         (2013.01)
    *A61B 17/12*       (2006.01)
    *A61F 2/82*         (2013.01)

(52) U.S. Cl.
    CPC ............ *A61F 2/95* (2013.01); *A61B 17/1214* (2013.01); *A61B 2017/1205* (2013.01); *A61F 2002/011* (2013.01); *A61F 2002/016* (2013.01); *A61F 2002/823* (2013.01); *A61F 2002/9534* (2013.01); *A61F 2230/0069* (2013.01); *A61F 2250/0039* (2013.01); *A61F 2250/0098* (2013.01)

(58) Field of Classification Search
    CPC ....... A61F 2002/823; A61F 2002/9534; A61B 17/221; A61B 17/1214; A61B 2017/1205
    See application file for complete search history.

(56) References Cited

U.S. PATENT DOCUMENTS

| | | | |
|---|---|---|---|
| 2003/0125764 A1 | 7/2003 | Brady et al. | |
| 2010/0114017 A1* | 5/2010 | Lenker | A61B 17/12118 604/96.01 |
| 2013/0304181 A1* | 11/2013 | Green | A61F 2/966 623/1.11 |
| 2014/0343585 A1* | 11/2014 | Ferrera | A61B 17/221 606/159 |
| 2015/0359549 A1 | 12/2015 | Lenker et al. | |

\* cited by examiner

CATHETER SYSTEM FOR TREATING VASCULAR AND NON-VASCULAR DISEASES

PRIORITY

This application corresponds to the U.S. National Phase of International Application No. PCT/EP2016/080988, filed Dec. 14, 2016, which, in turn, claims priority to U.S. Provisional Patent Application No. 62/396,787 filed Sep. 19, 2016, the contents of which are incorporated by reference herein in their entirety.

TECHNICAL FIELD

The present invention relates to a catheter system and methods of using such catheter system for the treatment of vascular and non-vascular pathologies. More specifically, the present invention is directed towards a catheter system for the actuation of a temporarily implantable member elastically deformable by hydraulic means.

BACKGROUND OF THE INVENTION

Vascular disease has been recognized as one of the major leading causes of death and morbidity in the Western world, and can be expected to be on the rise globally. Atherosclerosis is a specific type of vascular disease that can manifest itself in the accumulation of degenerative material along and throughout the inner linings of vessel walls, and can be accompanied by the formation of plaques comprising variable degrees of fatty, fibrous and/or calcified tissue over time. While the onset of disease may be asymptomatic at first, lesion formation, plaque deposition and subsequent growth can lead to substantial thickening and hardening of blood vessels over time, thereby causing successive reduction of lumen diameter, restriction of blood flow and impairment of vessel flexibility.

Atherosclerosis can occur anywhere in the human body, including the cerebral, carotid, coronary, renal, hepatic, aortoilliac, iliac, gonadal, femoral, and popliteal arteries and veins, and can be differentiated into neurovascular, coronary, or peripheral vascular disease, depending on the affected vascular regions of the body. While the human body can partially compensate the gradual impairment of vascular function by formation of collateral vessels to maintain blood supply to affected tissues and organs, due the progressive nature of the disease, circulatory condition can deteriorate to a stage where dependent organs become inadequately supported. This can lead to variable forms of increasingly worsening health conditions and associated complications over time. For cardiovascular disease, angina pectoris, myocardial infarction (MI) and congenital heart failure may result. Patients suffering from peripheral vascular disease often exhibit, in the order of disease progression, claudication, ischemic rest pain, ulcerations, and may develop critical limb ischemia (CLI), gangrene or tissue necrosis.

As opposed to the more prevalent forms of obstructive vascular disease, the circulatory system can develop other vascular defects that involve the abnormal dilation of blood vessels, such as the formation of aneurysms. Aneurysms are blood-filled vascular protrusions caused by the gradual weakening and subsequent dilation of vessel walls. These malformations can occur at vital regions throughout the human body, including the carotid arteries, aorta and brain. The weakened vessel walls can be susceptible to rupture, potentially resulting in acutely life-threatening complications, such as hemorrhaging, embolisms and strokes. Certain other types of vascular anomalies, such as the formation of a passageway between a vein and an artery, or arteriovenous (AV) fistula, can be congenitally acquired, originate from vessel trauma and inflammation, or be purposely created for therapeutic reasons as a specific form of vascular access for hemodialysis. Patients with AV fistulas or AV grafts may experience complications, such as thrombus formation, vessel narrowing and calcification, frequently requiring vascular intervention in the form of balloon dilation, stent placement, grafting, and/or removal of thrombotic matter to effect revascularization.

Currently, the interventional instruments available to physicians may be adequate; however, some procedural inefficiencies and limitations continue to exist due to the inherent limitations in product design and patient anatomical complexities. There is an unmet need to provide improved medical devices for treating both obstructive and dilative types of vascular diseases.

RELATED PRIOR ART

Depending on the individual clinical condition, weakened, dilated, malformed, narrowed, stenotic or occluded blood vessels can be treated in a number of ways, including the systemic administration of pharmaceutical agents and the local, minimally invasive application of medical devices that can be temporarily inserted or permanently implanted into the body of a patient. Vascular implants intended for permanent implantation can typically include balloon-expandable stents (BES), self-expandable stents (SES), flow diverters, stent grafts, and non-retrievable bioabsorbable devices, while devices designed for temporary deployment within the vascular anatomy may include balloon dilation catheters, scoring devices, atherectomy devices, retrieval devices, filters, embolic protection devices, temporary stents and equivalents.

To therapeutically address the various manifestations of obstructive vascular disease, angioplasty procedures can be performed. Balloon dilation catheters can generally be inserted, along a previously inserted guide wire, into a patient's blood vessel at a variety of different blood-vessel access points, including the femoral, subclavian, radial, pedal and brachial arteries. The balloon catheter can be advanced along the guide wire in order to position the inflatable portion of the catheter in or near a target region of the blood vessel. Upon placement, the balloon can then be inflated in order to mechanically dilate and displace a blockage, lesion, or other problem within the target region. To prevent a potential relapse or recoil of the treated target vessel region, tubular meshes, such as stents, stent grafts and scaffolds can be inserted to maintain an adequately sufficient luminal patency post-dilation. The standard form of treatment may comprise a pre-dilation of the target vessel, followed by stenting with a balloon-expandable or self-expandable stent. Direct stenting refers to the application of a stent to achieve vessel dilation and stabilization at substantially the same time without prior predilation. The high expansion pressure provided indirectly through the balloon member onto the diseased vessel segment can be advantageous for dilating severely stenosed and/or calcified lesions. Other treatment forms may include the release of a self-expandable stent subsequent to balloon dilation. While self-expandable stents are comparably more flexible as balloon-expandable stents, the amount of radial force exertable on the vascular surrounding to resist implant compression can be considerably lower.

The rupture of intracranial aneurysms can be a particularly catastrophic event, requiring immediate medical intervention on the order of minutes to prevent debilitating brain damage or death. Surgical techniques for the treatment of cerebral aneurysms typically involve a craniotomy requiring creation of an opening in the skull of the patient through which the surgeon can insert instruments to operate directly on the patient's brain. Once access to the aneurysm is achieved, the surgeon can place a clip across the neck of the aneurysm to achieve hemostasis.

Other alternative and minimally invasive procedures have been developed that involve the local delivery of liquid or solid embolic agents via a micro-catheter placed into the aneurysm sac, for forming an embolus capable of blocking the blood flow from the afferent vessel. Embolic agents in the form of vaso-occlusive coils are most frequently applied to treat cerebral aneurysms. Limitations in the ease of use and effectiveness of treatment may arise from unpredictable compaction due to variable hemodynamic blood flow conditions, sub-optimal packing density, and poor anchoring stability in wide-necked aneurysms. Thus the application of embolic agents may frequently require the co-administration of adjunct medical devices, including stents and embolic protection devices that help to stabilize an aneurysm neck during the delivery of the agent into the saccular region, as well as to prevent the inadvertent migration of embolic agents and coagulated matter into the vessel adjacent to the aneurysm.

Another minimally invasive approach can be performed by placement of flow diverters, stents, or stent grafts via a delivery catheter across the vascular region adjacent to an aneurysm, and within the lumen of the vessel. These device types can maintain the blood flow through the vessel while diverting and/or reducing blood flow/pressure applied to the interior of the aneurysm. The lateral sealing capability and treatment efficiency can be crucially dependent on the blood permeability of the deployed implant. Non-covered stents, while exhibiting a greater degree of flexibility and smaller crossing profile ideally suited for the access to narrow and tortuous vessels, may generally not be sufficient as a stand-alone treatment due to the inherently higher mesh size or implant porosity. Thus, they may not be capable of blocking an amount of blood sufficiently adequate to achieve clotting of the blood contained within the aneurysm. In consequence, such devices may require co-administration with vaso-occlusive devices, such as aforementioned coils, to achieve complete aneurysm occlusion. Stentgrafts on the other hand can typically exhibit an adequately low permeability capable of blocking the flow of blood to the aneurysm. However, as the latter devices are generally less flexible and exhibit a greater crossing profile, they can't be easily placed in more tortuous and narrow vessels, such as present in the brain. Further complications may arise from incorrect placement and existence of nearby collateral and/or branch-off vessels adjacent to the aneurysm that can provoke the risk of insufficient perfusion to other vital regions of the organ, thereby severely limiting their use in the cerebrovascular anatomy.

Concerning the application of the medical devices, both permanent and temporary implantable devices and/or their respective delivery/deployment devices can be activated by mechanical or other activation means, typically releasing a preset implant shape from a restrained, compressed, crimped, retracted or otherwise retained configuration towards an unrestrained, expanded, extended or otherwise unretained configuration. Most often, such types of implantable devices can comprise of shape-memory alloys formed into a self-expandable mesh. Shape release between a restrained and unrestrained configuration can imply that the shape and other properties are intrinsically 'built-in' (through design and material properties) prior to deployment and cannot actively be controlled either during and/or after deployment or both (see for example U.S. Pat. No. 5,026,377).

When intended for temporary deployment, these device types can additionally incorporate means for retrieval. Such means may include a tethered construction that utilizes a set of one or more strings attached to a proximal and/or distal device portion or both through which the device can be retrieved post-deployment, for example, into a tubular retainer (see for example WO 2009/114046 A2). Other types may incorporate an attachment means that can be reversibly coupled to the parent (deployment) device to facilitate device retrieval, such as a hook, a bayonet mechanism or equivalent mechanical coupling means (see for example U.S. Pat. No. 5,607,466). Still other expandable device types, including those formed from braided members, may utilize a mechanical means for device retrieval, such as rigid elongated members coaxially received across a length portion of a braided member and catheter shaft, and attached to one or more portions thereof. For example, state of the art flow diverters, temporary stents, filters, embolic protection devices and equivalents can typically comprise of a self-expandable mesh tethered to the working end of a delivery device, such as a catheter.

Contemporary SES intended for permanent implantation, however, are typically not capable of partial or complete device retrieval. Once such a device has been completely released from a retaining mechanism by the physician, no in-situ means for device retrieval and/or reversal of the deployment procedure exist. This seemingly unfavorable behavior necessitates strict positional control by the physician to avoid irreversible device misplacement. The situation can become further complicated in that SES may exhibit variable degrees of foreshortening. As a result of foreshortening, the length of an undeployed stent can differ substantially from the length in deployed state, thereby increasing the likelihood for off-target stent placement issues. Further, upon initiation of the (often unilateral) release procedure, a SES may begin to distally open and anchor in the surrounding vessel, without being fully released length-wise. Continuing retraction of the stent retaining mechanism or movement of the catheter system while the stent is only partially deployed can not only lead to an undesired off-target-center shift in stent position, but may further be accompanied by vessel trauma. In consequence, misplaced SES can require surgical intervention as an ultimate means for device removal.

For delivery purposes, the self-expandable mesh can be coaxially placed between an inner member and outer, retractable sheath. The outer sheath in extended state maintains the mesh in a compressed state (see for example U.S. Pat. No. 5,626,602). By retraction of the outer sheath, the pre-set mesh structure can be expandably released, usually initiated from the distal end of the mesh. The described effects can be utilized for the release and/or deployment of self-expanding stents within designated target vessel geometries. In SES catheter systems, a self-expandable stent structure can be physically restrained within a tubular outer member or sheath (the process often termed as "loading" of a stent into the delivery device) prior to deployment. Upon proximal retraction of the restraining tubular outer member or sheath within the target vessel (the process often termed as "release" of a stent from the delivery device), the compressive mechanic energy stored in the SES can cause it to return to its nominal shape, or until it reaches a balancing equilibrium with the resistive radial force exemplarily exerted through a surrounding vessel wall surface. As such, the amount of radial expansive and/or compressive force that can be generated by a self-expandable stent within a target vessel can be severely limited, and neither actively controlled nor adjusted in-vivo. Contemporary SES delivery systems do not exhibit an active means to increase the radial force of the stent member post release. While some of these devices may make use of axial loads to effect an axial and/or radial extension and compression of a braided member, the majority of mechanical solutions is directed towards the operation of the shape retaining mechanism. Further, the presence of a rigid member can introduce an additional stiffness element across the instrument length, thereby negating maneuvering in delicate and tortuous vascular regions, such as the brain.

The amount of remaining outward radial force after stent deployment is primarily dependent on the radial disparity between the nominal SES diameter and the target vessel diameter. Within acceptable physical margins, through the passive choice of nominal device dimensions and parameters pre-set by the manufacturer, physicians can radially overextend the target vessel in order to maintain a desired radial pressure on the vessel wall surface, thereby achieving a desired degree of luminal patency and/or vessel wall stabilization, and preventing a relapse of the treated vessel. However, the presence of a chronic outward force can have detrimental effects on the long-term outcome of the therapeutic intervention, frequently leading to continuously present vessel wall irritation, inflammation, undesired neointimal growth and subsequently, restenosis of the affected vascular segment, necessitating re-intervention. Additionally, there can be a design limit as to how much radial force can be passively exerted onto a diseased vessel wall through the comparably flexible SES implant by itself without additional dilatation, particularly in the presence of severe tissue hardening and/or calcification.

Under such circumstances, balloon-expandable stents (BES) can remain a more adequate therapeutic option, as the stent structure can be actively supported and propagated into the hardened, calcified tissue during the dilation process. Balloon dilation and direct stenting using a BES can be facilitated at significantly higher pressures of approximately up to 15-25 bar, as compared to SES release in the absence of a balloon. However, certain drawbacks can persist over SES systems. During balloon application, blood flow within the treated vessel can remain blocked until the balloon is deflated and removed from the treatment area. Once the balloon is removed, the BES structure can be prone to a certain extent of recoil, effectively reducing the amount of radial force that can be exerted onto the vessel wall post-deployment. This can result in undesired dimensional disparity, and may manifest itself in potential migration issues, ultimately affecting the efficiency of the stent placement. Additionally, as BES can be generally more rigid, and at the same time plastically deformable when subjected to load conditions in the vasculature, their use can often be restricted to protected vessel anatomies, i.e. such that are sufficiently devoid of motion and external forces.

Concerning the constructional characteristics, different types of medical implants can be constructed of various metal or metal alloy substrates for forming a structural support, including Titanium, Tantalum, Cobalt-Chromium, Nitinol, and Stainless steel. A substantially biocompatible material can be selected as the first level of control in forming the basic substrate configuration by employing exemplary materials listed above. Although these commonly used biocompatible materials may provide adequate mechanical/structural properties in a majority of situations, it may be desirable in certain clinically demanding applications to provide an "additional layer of coverage" by overlaying the outermost substrate with a second biocompatible material that can be optimized and homogeneously formulated for specialized clinical applications. In the case of stent grafts, covered stents and vascular scaffolds, this "additional layer of coverage" can be implemented as a membrane component that can be adjoined with a stent support. On a functional level, the "membrane" component of a stent graft provides a physical barrier against leakage of blood and inappropriate intraluminal cellular growth, and the "stent" component can mechanically support the treated vessel wall and fixate the thrombi/treated lesion. The membrane component can be utilized to selectively seal off adjacent vessel walls from intra- or extravascular blood flow, which can be suitable for treating de novo lesions, perforations, dissections, ruptures, fistulas, aneurysms and related conditions. For example, endovascular devices such as covered stents, stent grafts, or vascular scaffolds can be effectively utilized for restoring and improving the patency of protected peripheral arteries, as well as treating iliac artery stenosis (i.e., abnormal narrowing of blood vessels) in patients suffering from de novo or restenotic lesions of the common and external iliac arteries among other conditions.

Depending on the intended application, the membrane component of medical devices can be composed of modified natural products, metals, ceramics, organic and inorganic materials, modified natural and synthetic polymers. A combination of modified natural products and synthetic polymers can exhibit improved physical and mechanoelastical properties. The incorporation of one or more polymeric materials, including derivatives composed of medical-grade fluoroelastomers, polysulfones, polyamides, polyurethanes, polyesters, polyethers, and silicones, can enhance the structural properties and performance attributes of advanced medical devices. For example, most commonly utilized synthetic or modified natural polymeric "biomaterials" include without limitation: polyurethanes, polycarbonates, polyurethane carbonates, polyesters, polyamides, polyimides, polyvinyls, polyolefins, Teflon™, Gore-Tex™ (a type of expanded polytetrafluoroethylene), Dacron™, polyvinyl alcohols, polyethylene oxides, polyacrylates, polymethacrylates and polycyanoacrylates, latex, polyvinyl chlorides, hydrogel forming agents such as PHEMA, hyaluronic acid, chitosan, alginate, dextrane, cellulose, and derivatives thereof. These materials have been utilized for constructing various components for the manufacture of various endovascular devices, including stent grafts, covered stents, vascular scaffolds, synthetic vessels, and filtration devices. A stent graft can be noninvasively administered to the site of a damaged vessel by using a delivery catheter, precluding the surgical removal of any existing vascular tissue or vessels. In some urgent situations such as an imminent rupture of an aneurysm, a stent graft can be conveniently deployed as a bail-out device for treating emergent or acute life-threatening conditions such as the threat of terminal bleeding. In contrast, when the removal and replacement of an entire section of a vessel may be necessary, an invasive "bypass" surgical procedure can be performed involving the implantation of a synthetic vessel as a functional substitute for an irreversibly damaged vessel, and thereby, restoring adequate blood flow to the treated region.

To describe the various designs and approaches that have been developed for manufacturing endovascular devices, referenced (interchangeably) by persons skilled in the art as "stents," "stent grafts," "covered stents," "grafts" or "vascular scaffolds", some examples are described briefly below in order to further distinguish the endovascular devices of the present disclosure under the Detailed Description subsection:

(a) A Balloon Expandable Covered Stent ("BECS") can be configured by welding together two flexible stents separated by a single layer of an expandable polytetrafluoroethylene ("ePTFE") graft material in a "stent-graft-stent" configuration. Commercial examples include the "Jostent PSG" for peripheral applications and the "Jostent Graftmaster" for coronary applications, as described by U.S. 5,916,264. Alternatively, BECS can be configured by welding together a single flexible stent inserted between two ePTFE graft membranes in a "graft-stent-graft" configuration. Commercial examples include the "Atrium Advanta" for peripheral applications, for example, as described in US 2005/055081 A1.

(b) A single ePTFE graft membrane can be attached to a single stent by mechanical fixation between superimposing stent struts. Commercial examples include Bentley Innomed's "BE graft" and "Be stent," for example, as described in US 2013/317595 A1.

(c) A self-expandable covered stent ("SECS") can be configured by affixing an ePTFE liner to an endoskeleton or exoskeleton nitinol structure, in which the seams and/or sutures can be formed by mechanical fixation techniques. Commercial examples include Viabahn and Hemobahn from Gore, in which a durable, reinforced, biocompatible ePTFE liner can be attached to an external nitinol stent structure intended to produce a self-expandable covered stent.

(d) An encapsulated endovascular device can be configured by encapsulating with microporous polyurethane-silicone, a polymer-based graft material by utilizing dipcoating techniques. Commercial examples include the "Wallgraft," developed by Schneider, for example, as described in EP 0 659 389 A1 and U.S. Pat. No. 6,375,787.

(e) An encapsulated endovascular device can be configured by forming a film of polytetrafluoroethylene graft by electrospinning processes, thereby creating an inseparable, encapsulating, fibrous, non-woven mesh, for example, as described in US 2013/238086 A1.

In general, the construction of these endovascular devices exhibit the following similarities: (1) specific stent structure and design; (2) pre-formed membrane; and (3) co-fixation of dissimilar materials. For illustration, a typical SECS or BECS can be constructed of three components as described below:

(1) Braided Member/Stent Component: A braided member/stent can consist of implantable, surgical grade metal alloys, including without limitation CoCr (L605), Elgiloy, Phynox, NiTi, MP35N or SS316L. Braided members can be manufactured preferably from spring-metal and/or shape memory alloys, braiding one or more individual wire filaments at a desired angle onto a typically cylindrical mandril having an initial diameter. The braid, as wound may then be cut to a desired length and transferred onto a desired shape to perform additional adjustments in terms of length, diameter, spacing density, angle variation and shape. The braid can then be heat-treated to relieve residual stresses built up during manufacturing operations and lock the structure into a nominal shape. Non-wire based stents can be manufactured from a hollow metal tubing of defined inner diameter and wall strength using precision laser technology. Further processing can include mechanical and chemical operations, such as electropolishing, to achieve the desired dimensions and surface quality of the finished stent.

(2) Membrane Component: A graft membrane can be inserted between one or more stent components as a means of fixation. Welding points can be placed at the proximal and distal stent ends (also referenced as crowns) so that the graft membrane can be enclosed and fixated between two superimposed stent components in order to form a single, non-separable device. Suitable materials include without limitation: synthetic biocompatible polymeric materials such as expanded PTFE ("ePTFE"), polyethylene terephtalates ("PET"), elastomeric polyurethane carbonates ("PUC"), polyurethanes, the equivalents and derivatives thereof, and biologically derived materials, such as horse pericard.

(3) Delivery System: An endovascular device, such as a balloon-expandable or self-expandable stent, can be crimped onto the balloon portion of a PTA catheter, or respectively placed into a distal retaining element of a delivery catheter to form a Stent Delivery System ("SDS"). While their individual actuation and delivery method may differ, both types share in common, that the endovascular device is permanently released at the site of treatment. For endovascular devices not intended for permanent release, actuation mechanisms for the distal working end and/or endovascular device typically comprise of mechanically based solutions, such as a) wire type, b) rod/tube type or c) spring-assisted types. In either case, the described activation mechanisms and involved mechanical forces exerted due to the pulling of a wire or sheath, pushing of a stiff tube or activation of a spring-assisted mechanism (e.g. for expending a deformable cuff or allowing a self-expandable stent member to expand) impose certain operational drawbacks further detailed below.

Aforementioned conventional stent delivery systems generally comprise a handle portion and an elongated shaft, wherein the stent is disposed within a delivery portion at the distal end of the shaft. To deploy the stent, an outer sheath is provided that can be retracted relative to the stent to release the stent from its delivery configuration. Inherent to its construction, the sheath in such systems spans a considerable length portion of the catheter, resulting in an increased profile and stiffness along the length of the catheter. As the outer sheath requires an operational margin or actuation distance to release the stent, both profile and stiffness of the instrument are discontinuous in nature, lowering bending resistance along the transition regions of inner shaft and outer sheath, and impeding both pushability and maneuverability of the instrument through a tortuous luminal system of a patient. Yet still, because the sheath is situated around an inner catheter shaft there is an increased risk of the sheath unintentionally adhering to such components of the catheter during operation, resulting in suboptimal actuation of the sheath and deployment of the stent.

A correlated issue with such delivery systems is that an outer sheath exerts a constant compressive force onto the retained stent, thereby causing the stent to gradually embed itself into the outer sheath during storage. The accompanying increase of the static frictional force between components can be particularly problematic, because the outer sheath is typically pulled back in a 1:1 ratio with the user's physical strength, or force. As the amount of force that is required to retract the sheath scales in proportion to the length of the stent, the force may become so substantial, that the physician operator cannot predictably distinguish between the reaching of a desired release force threshold or device malfunction. Ideally, the physician user should be enabled to controllably retract the sheath in a continuous fashion, utilizing a moderate and constant amount of force, to accurately position the stent with minimal trauma. However, the initial tension built up along the length of the instrument to overcome the static regime of friction, combined with a discontinuous or sudden movement, can result in a catastrophic discharge of mechanical energy, risking device buckling, implant misplacement, tensioning of the vascular anatomy and substantial vascular trauma, to the detriment of the patient.

US 2013/0304179 A1 constitutes an improved stent delivery system, disclosing a catheter having a retractable sheath attached to a hydraulic actuator. The catheter comprises an outer tubular member being projectable proximally upon hydraulic force to effect the release of a restrained self-expandable stent member. While the catheter described in US 2013/0304179 A1 improves upon shaft stiffness and device profile issues persistent in the prior art, the construction does not address entirely the described operational issues arising from the contact pairing of the stent (implantable member) with an outer sheath, the associated frictional tension that can build up between these instrument components during operation, sufficient stability of components and accordingly, the controllability of release.

Taken together, the current state of the art catheter systems do not unequivocally resolve the issues related to a safe and efficient permanent delivery or temporary deployment of implantable members. There is a particular need to provide a) highly flexible, temporary implants with an adequately small crossing profile for enabling access to substantially narrow and tortuous vascular regions of the body, wherein b) the deployment devices can be safely and accurately positioned within the desired target anatomy, and wherein c) the devices can facilitate reversible dimensional adaption to the underlying vascular anatomy without risk of in-vivo device misplacement and/or vascular trauma, and wherein d) the device exhibits a sufficiently small lateral mesh size or porosity to effectively divert from and/or block the blood flow to a diseased vascular segment while adequately maintaining the intraluminal blood flow to healthy vascular regions and dependent vital organs at substantially the same time, and e) wherein the devices can function to controllably assist or to replace standard vasoocclusive therapy of aneurysms. Further still, there is an apparent unmet need to provide a self-expandable, temporary implantable member capable of providing an increased, actively controllable radial force to diseased regions of the body in need of treatment.

One object of the present invention is to provide a device that can combine the flexibility of a self-expandable stent with the capability of delivering an in-vivo adjustable, enhanced radial force near equivalent to a balloon-expandable stent and superior to a self-expanding stent, while being capable of selectively diverting and/or reducing blood flow to select vascular regions similar to a stent graft. Such a device can be perceivably beneficial in the treatment of both obstructive and is dilative forms of vascular disease, and can constitute the ideal therapeutic implement to treat vascular malformations, such as aneurysms in the brain.

SUMMARY OF THE INVENTION

The present invention provides a catheter system for the actuation of a temporarily implantable member elastically deformable by hydraulic means, wherein the device is capable of providing an actively and in-vivo controllable amount of radial pressure to a vascular segment in need of treatment, and wherein the applicable radial pressure range can be sufficiently adequate to effectively treat a range of diseased vessel conditions, including severely hardened and calcified tissue; and wherein the device is capable of conformably adapting in-vivo to a variable vascular anatomy in a continuous manner. Axial hydraulic actuation of the implantable member confers the ability to controllably maintain the blood flow within the diseased vessel segment during time of treatment; the ability to provide structural vessel support, shielding and/or fixation functionality; and temporary flow diversion and/or filtering capabilities, including the capture and extraction of foreign bodies and ablated materials. Various embodiments are directed to methods for manufacturing the HATS ("Hydraulically Actuable Temporary Scaffold") catheter system disclosed herein. Various embodiments are directed to methods for treating vascular and/or non-vascular diseases utilizing one or more disclosed "HATS" configurations for facilitating several therapeutic functionalities, including improved: (a) flow diversion; (b) vessel shielding, support and stabilization; (c) vessel repair; (d) vessel dilation;

(e) lesion treatment; (f) occlusion of vascular defects and hemostasis; (g) scoring; (h) debulking; (i) embolic protection; (j) capture and retrieval; (k) coiling assist.

DETAILED DESCRIPTION

Terms and Definitions

Figure 1:
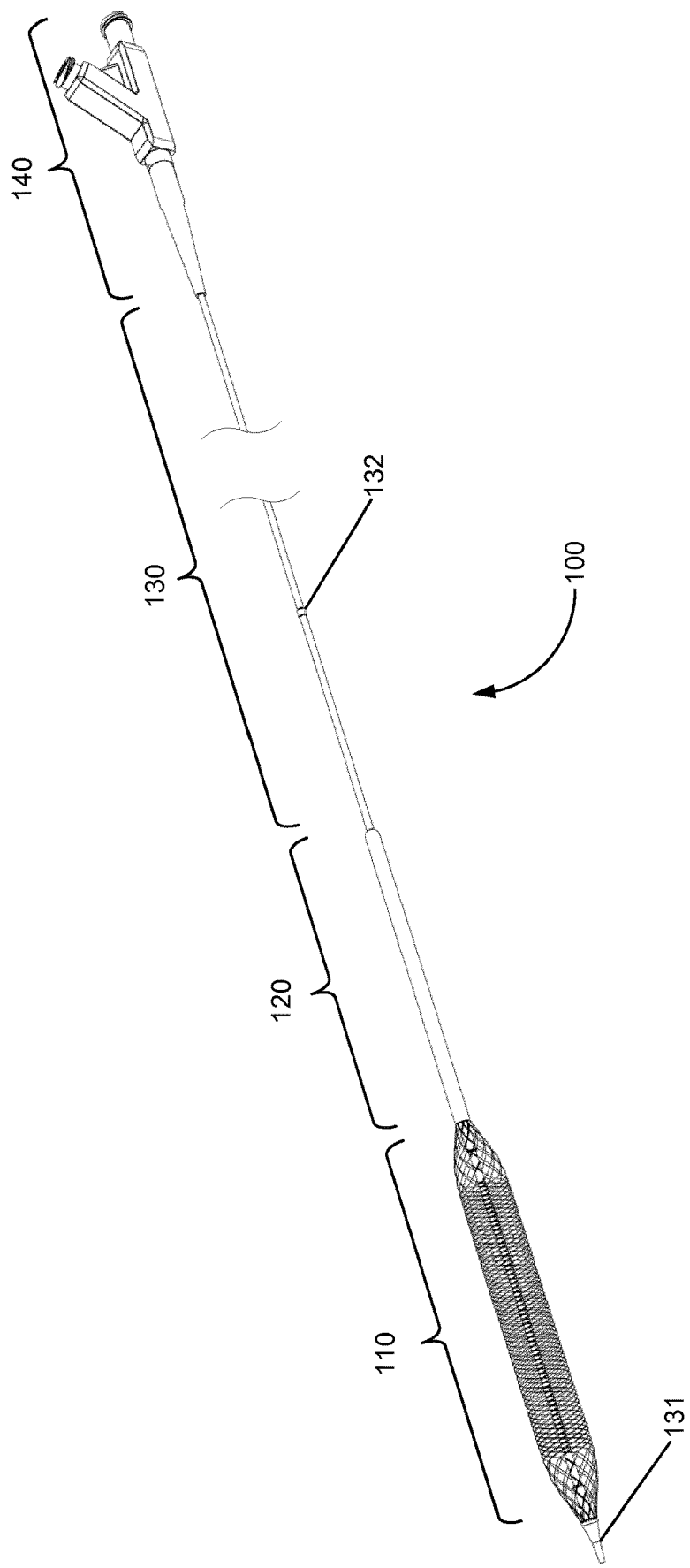
FIG. 1 illustrates a perspective view of the HATS catheter system of the present disclosure in a deployed state, as an embodiment.

The term "Hydraulically Actuatable Temporary Scaffold" ("HATS") refers to various embodiments and configurations of the distal working end of a catheter system comprising an implantable braided member elastically deformable by hydraulic means disclosed herein.

When used herein, the term "temporary" refers to a non-permanent, transient, and/or intermittent application of a medical device incorporating means for removal from a treatment site following its application.

The term "medical device(s)" includes any "endovascular devices" or "non-endovascular devices" as defined and described hereafter.

The term "endovascular devices" refers to medical devices, implants, and/or synthetic vessels comprising any number of components, which can be inserted, in part or entirely, into selective tissues, vessels, organs, and/or deposited into the cavities of patients for various diagnostic, therapeutic, and/or cosmetic procedures/interventions. Exemplary "endovascular devices" for vascular intervention include without limitation: stents, stent grafts, covered stents, vascular scaffolds and synthetic blood vessels, vascular shunts such as arterial, venous and arteriovenous (AV) shunts, ventriculoperitoneal (VP) and transjugular intrahepatic portosystemic shunts (TIPS), vascular stents, such as coronary stents, peripheral stents, neurovascular stents, renal stents, iliac artery stents, carotid stents, below-the-knee (BTK) stents, superficial femoral artery (SFA) stents, inferior vena cava filters (IVC) and embolization coils. These endovascular devices can be utilized for treating various vascular diseases and conditions including (without limitation): atherosclerosis, obstructive vascular diseases, plaque formation, partially or completely blocked, stenosed and/or obstructed vessels, ruptures and dissections, impaired vessels at the indicated vascular locations, thoracic abdominal aneurysm (TAA), abdominal aortic aneurysm (AAA), and coronary artery bypass (CAB).

The term "non-endovascular devices" refers to any tangible device (devices, implants, instruments, equipment and/or prosthetics) comprising any number of components, which are not to be inserted, in part or entirely, into selective tissues of an organism or deposited into the cavities of organisms, but which can be used for various diagnostic, therapeutic, and/or cosmetic procedures/interventions Exemplary implantable non-endovascular devices include without limitation: gastrointestinal stents such as biliary duct stents (e.g., for treating bile duct obstructions) and esophageal stents (e.g., for treating esophageal obstructions, e.g., as caused by esophageal cancer); respiratory products such as endotracheal tubes and tubes used in ventilator/respirator circuits; urologic products such as prostate stents, urethral stents, and lacrimal duct stents. The combination of non-endovascular and vascular applications, or corporeal and extracorporeal applications is possible, in terms of the patient's body (i.e. through the skin using needle puncture, for enabling vascular access) acting as an 'interface' to extracorporeal applications.

The terms "braided member," "wire stent," "wire scaffold," or "stent" can be interchangeably used herein to refer to an endovascular device comprising a metal structural support. The terms "covered stent," "stent graft," "graft," or "vascular scaffold" can be interchangeably used herein to refer to an endovascular device comprising a metal structural support (e.g., stent) and a membrane component providing at least a filtering function. These devices can be described in other references by alternative terms such as "covering," "graft," "scaffold," "membrane," "matrix," "web," "sheet," "layer," and/or "film."

The term "membrane" refers to a "structure, having lateral dimensions much greater than its thickness, through which transfer may occur under a variety of driving forces." PAC, Vol. 66, No. 8, page 1671, "Thin films including Layers: Terminology in Relation to their Preparation and Characterization" (IUPAC Recommendations 1994). Membranes can function as a selective barrier that can permit the passage of certain "permeable" constituents through, and can selectively retain "non-permeable" constituents that cannot pass through the membrane. The degree of selectivity and permeation characteristics of a membrane depends for example on the average membrane pore size, size distribution, spatial arrangement, pressure differential and membrane material-permeate interaction. Depending on the pore size, they can be classified as microfiltration (MF), ultrafiltration (UF), nanofiltration (NF) and reverse osmosis (RO) membranes.

The terms "microporous," "mesoporous," and "macroporous" refer to pore size ranges of about ≤2.0 nm, 2.0≤50 nm and ≤0.05 μm, respectively, according to standard definitions established by physical chemists. Pure & Applied Chemistry (PAC), Vol. 31, No. 4, page 585, "Manual of Symbols and Terminology for Physicochemical Quantities and Units, Appendix 11: Definitions, Terminology and Symbols in Colloid and Surface Chemistry)".

The term "coating" refers to a "film" defined as a "condensed matter restricted in one dimension," according to standard definitions established by physical chemists. Pure & Applied Chemistry (PAC), Vol. 66, No. 8, page 1671, "Thin films including Layers: Terminology in Relation to their Preparation and Characterization" (IUPAC Recommendations 1994). The terms "nanoscopic film, microscopic film and macroscopic film should apply specifically to films which have lateral dimensions in the range of several 0.1 nm [5]-100 nm, 0.1-100 µm and above 100 µm, respectively," according to PAC, Vol. 66, No. 8, page 1671. The terms "nanometer thick film, micrometer thick film, millimeter thick film, etc. must refer specifically to film thicknesses in the ranges 0.1-100 nm, 0.1-100 µm, 0.1-100 mm, respectively," according to PAC, Vol. 66, No. 8, page 1671. In general terms, a "coating" differs from a "layer" and a "membrane" in that the entirety of the "coating" material is completely affixed to an underlying surface composed of another material such that there is no separation between a "coating" and the surface on which the "coating" is attached.

The term "layer" refers to "any conceptual region of space restricted in one dimension, within or at the surface of a condensed phase or a film." PAC, Vol. 66, No. 8, page 1671, "Thin films including Layers: Terminology in Relation to their Preparation and Characterization" (IUPAC Recommendations 1994).

The term "incorporating" refers to the structural integration of polymers into suitable vascular support structures of interest, in which a polymer composition can be incorporated as components of fibers, films, membranes, meshes, sieves, mats, or equivalents known to persons skilled in the art, and/or combinations thereof.

The terms "encapsulating," "enveloping" and "blending" can be used interchangeably to refer to the enclosure of substrate material(s), partially or entirely, by employing a polymer composition of one or more polymers. A graft material is not limited as to the exact disposition of a polymer matrix, for example, the polymer matrix can be incorporated, adhered, layered, reacted, blended/mixed, embedded, grafted, bonded, crosslinked, copolymerized and/or reacted with an intermediate layer that can be adhered, adjoined, affixed and/or reacted, or combined with other conventional biomaterials in any manner. Further, the polymer composition can be combined with a conventional biomaterial, and the combination can be adhered onto or around or within a device or a surface such that the polymer composition and biomaterial can be deposited simultaneously or sequentially. This disclosure contemplates the co-formulation of any biomaterial, including bioactive agents and a polymer composition, or the incorporation of a polymer into a biomaterial or medical device.

The terms "foam(s)," "fibre(s)," "sponge(s)," refer to a three-dimensional matrix composed of any material, including polymers that can be produced by any method known to persons skilled in the art.

The term "spray(s)" refers to any dispensing equipment that can be employed to deploy solid particulates or liquid droplets comprising a polymer composition in order to deposit in situ these polymers on top of a target substrate.

The terms "spinning" or "spun" refer to any dispensing equipment that can be employed to deploy solid fibers or liquid jets comprising a polymer composition in order to deposit in situ these polymers over a target substrate.

The term "crosslinking" refers to a "reaction involving sites or groups on existing macromolecules (i.e., natural and/or synthetic polymers) or an interaction between existing macromolecules that can result in the formation of 'a small region' in a macromolecule from which at least four chains emanate. The small region may be an atom, a group of atoms, or a number of branch points connected by bonds, groups of atoms, or oligomeric chains. However, 'a reaction of a reactive chain end of a linear macromolecule with an internal reactive site of another linear macromolecule results in the formation of a branch point, but is not regarded as a crosslinking reaction.' "PAC, Vol. 66, No. 8, page 1821. The general effect of crosslinking is reduced flexibility, increase in mechanical stability, and increase in melting point for synthetic polymers.

The term "protective barrier" refers to any physical barrier that can prevent the loss of fluid from damaged blood vessels; reduce bleeding; prevent further physical damage; reduce inflammation; promote healing; enable embolic protection; promote or prevent blood clotting; promote or prevent adhesion to tissue surface; promote de novo collagen formation; promote tissue regeneration; promote innervation; promote vascularization; decrease the period for healing, and/or promote cellular growth rates; prevent scarring; prevent viral, microbial, fungal infection; protect from extreme environmental conditions, including extreme heat and cold temperatures; protect from the entry of environmental water; and reduce pain.

The term "embolic protection" refers to the therapeutic use/application of specific "embolic protection devices" that can be appropriately configured and used to capture and remove debris that becomes dislodged during an interventional procedure. For example, there can be a significant risk of distal embolisation caused by the release of particulate matter, including plaque debris such as fibrin, necrotic atheromatous core, foam cells, cholesterol clefts, and thrombi during and after performing balloon inflation or stent deployment. When the therapeutic spectrum is extended to specifically include the debulking, capture and removal of considerably larger thrombotic masses, such devices can be more appropriately referred to as "thrombectomy devices". Within the context of this disclosure, the endovascular devices of this invention can be selectively configured to include embolic protection and thrombectomy capabilities. The term "aneurysm closure" refers to the therapeutic use/application of specific "aneurysm closure devices" that can be appropriately configured and used to selectively seal off the afferent and efferent vessels of an aneurysm sac either as stand-alone or co-administered medical device for rendering therapeutic treatment. In regard to the capability of such devices to selectively close, divert and/or modulate the flow of blood within and between vessels of a treatment site, such devices can interchangeably be referred to as "flow diverters".

Catheter System

The catheter system of the present invention can impart an actively controllable axial hydraulic load onto a temporarily implantable member, such as a braided member, via a longitudinally displaceable hydraulic chamber coaxially integrated into the catheter system. The chamber can be charged with variably is adjustable amounts of pressures ranging from below to above atmospheric pressure by means of an attachable standard inflation source. The variable axial hydraulic load imparted on the braided member can be adjustably transformed into an enhanced radial force contribution to effectively treat complex lesions normally considered untreatable by standard self-expanding stent systems. Further, the variably adjustable axial load can impart a pre-determinable geometric deformation capability to the braided member so that the implantable member can be conformably adjusted in-vivo to the dimensions of the vascular region to be treated prior to, during and/or after deployment. As the radial force exerted through the braided member onto the surrounding vessel wall can be adjustably increased and/or decreased in a continuous manner, enhanced means for structural vessel support, stabilization and/or fixation can be provided.

The present invention therefore relates to a catheter system (100), comprising:
- a catheter shaft (130) including a distal catheter tip portion (131);
- a hydraulic chamber (120) capable of transitional displacement along a longitudinal axis of the catheter shaft (130);
- a temporarily implantable member (110') located between the catheter tip portion (131) and the hydraulic chamber (120);
- characterized in that the transitional displacement of the hydraulic chamber (120) exerts force on the temporarily implantable member (110').

Any suitable temporarily implantable member (110') known to the person skilled in the art can be used in the catheter system of the present invention. A suitable temporarily implantable member is, for example, a braided member (110) which is extensible along the longitudinal axis of the catheter shaft (130). In a preferred embodiment, the braided member is bi-directionally extensible along the longitudinal axis of the catheter shaft.

In the following description, the catheter system according to the invention will be described with reference to the braided member. Nevertheless, this description is not intended as being limiting but any other temporarily implantable member can be used instead of the braided member where appropriate.

The implantable braided member of the present catheter system can be manufactured from radiopaque shape memory alloy, spring-metal, or rigid polymer based wire filaments that can be wound at a predeterminable braiding angle into a helical braided mesh of counter-rotating wire pairs. The overlapping struts can form diamond shaped cells with definable mesh size and surface area, or coverage. By imparting an axial hydraulic load onto the described braided mesh structure, the axial and radial distances of the diamond shaped cells can be controllably changed, thereby leading to a variably adjustable mesh size and surface coverage. This mesh deformation capability can be applied at various desired stages of the interventional procedure to controllably change the permeability of the lateral mesh surface, thereby providing a means to control hemodynamic flow conditions within a vascular region, i.e. to effect flow diversion or regulate the amount of blood transferable between vascular regions. At substantially the same time, the controllable mesh size can facilitate the selective capturing of foreign bodies of variable sizes, and ease removal thereof from the target treatment area. These selective filtering capabilities can be applied for embolic protection or debulking (plaque removal) purposes.

Usual catheter systems including catheter shafts and braided members and in particular the materials from which these devices can be prepared as well as their usual dimensions are known to the skilled person and can be selected according to the specific requirements. Useful materials and construction details are disclosed in US 2013/0304179 A1, the content of which is incorporated herein by reference.

The hydraulic chamber capable of transitional displacement along the longitudinal axis of the catheter shaft usually has a diameter being larger than the diameter of the catheter shaft. Furthermore, also the diameter of the braided member in extended form (see FIG. 4A) usually is smaller than the diameter of the hydraulic chamber. Therefore, the hydraulic chamber can have the largest diameter of all parts of the catheter systems being introduced within the patient's body. However, to enable access to vascular regions of increasingly smaller diameter, it can be perceivably advantageous to position the hydraulic chamber not in direct proximity to the braided member, but closer towards or at the proximal end of the catheter shaft, to utilize the smaller crossing profile of the catheter shaft. Thus, in another embodiment of the present invention, the catheter system comprises an extension member between hydraulic chamber and the braided member, wherein the transitional displacement of the hydraulic chamber exerts force on the braided member via the extension member.

The extension member can be for example an outer tubular shaft which surrounds the catheter shaft and which is located between the proximal end of the braided member and the distal end of the hydraulic chamber. The extension member length can be provided adapted to an individual clinical indication and/or access site.

As described above, the hydraulic chamber can be charged with different amounts of pressures ranging from below to above atmospheric pressure, which can result in a transitional displacement of the hydraulic chamber towards the distal or proximal end of the catheter shaft. For example, if the self-expandable scaffold is a braided member, the force exerted by the hydraulic chamber on the braided member can be such that the braided member is "pulled" into an extended form (see FIG. 4A) by applying a low pressure, such as a pressure below atmospheric pressure, to the hydraulic chamber. Such low pressure moves the hydraulic chamber towards the proximal end of the catheter shaft thereby exerting a force on the braided member, which pulls the braided member into its extended form.

If the pressure in the hydraulic chamber is increased, for example to about atmospheric pressure, the hydraulic chamber moves towards the distal end of the catheter shaft thereby exerting a force on the braided member, which allows the braided member to move into its nominal/resting form (see FIG. 4B).

Further increase of the pressure in the hydraulic chamber will move the hydraulic chamber further towards the distal end of the catheter shaft thereby exerting an increased force on the braided member which due to this force takes its compressed form as shown for example in FIG. 4C.

In case that it is not intended that the hydraulic chamber pulls on the braided member, it is not necessary that the braided member is affixed to the hydraulic chamber or the extension member there between. However, in a preferred embodiment of the catheter system of the present invention, the distal end portion of the braided member is affixed to the catheter tip portion and/or (preferably and) the proximal end portion of the braided member is affixed to the distal end portion of the hydraulic chamber or the distal end portion of the extension member. In this case, the braided member is directly or indirectly affixed between the distal catheter tip portion and the hydraulic chamber so that the transitional displacement of the hydraulic chamber along the longitudinal axis of the catheter shaft can pull the braided member into its extended form or compress the braided member into its compressed form.

For transitional displacement of the hydraulic chamber along the longitudinal axis of the catheter shaft hydraulic fluid is pressed into the hydraulic chamber or withdrawn out of the hydraulic chamber. The catheter shaft therefore includes a hydraulic lumen which allows transport of the hydraulic fluid from the proximal end of the catheter shaft to the hydraulic chamber. The hydraulic lumen can also include a coaxially arranged guide wire lumen extending from the proximal to the distal end of the catheter shaft. Alternatively and preferably, the catheter shaft contains two lumens, one for the hydraulic fluid and another one for the guide wire. The hydraulic fluid can be pressed into or withdrawn out of the hydraulic chamber via the hydraulic lumen using usual equipment attached to a manifold at the proximal end of the catheter shaft.

The catheter system of the present invention including specific and preferred embodiments will now be described in more detail with reference to the attached figures which are not intended to be limiting.

FIG. 1 illustrates a perspective view of the catheter system of the present invention in a deployed state, as an embodiment. In FIG. 1, the Hydraulically Actuatable Temporary Scaffold catheter system (HATS) 100 comprises a longitudinally extensible braided member 110, a hydraulic chamber 120 capable of translational displacement about the longitudinal axis of the catheter shaft, a dual-lumen configured catheter shaft 130, an end stop 132 mechanically delimiting the proximal motion of the chamber, and a manifold 140 for effecting guide wire passage and fluid transport to the hydraulic chamber. Braided member, hydraulic chamber casing and proximal end stop can be coaxially formed around the catheter shaft, wherein the braided structure can be provided distally affixed to a catheter tip portion 131 and proximally joined to a portion of the hydraulic chamber casing. During operation, the hydraulic chamber can be controllably charged with variable amounts of hydrostatic pressure, thereby effecting simultaneous movement of the proximal end of the braided member and hydraulic chamber casing about the catheter length axis. The hydraulic actuation mechanism enables placing well-defined negative and positive axial load (force) onto the braided member, resulting in seamlessly variable degrees of axial elongation between substantially extended, nominal, and substantially compressed states. The 'nominal' state of the braided structure can be equivalent to a design specification and refers to nominal length and diameter of the braided member in an axially unloaded or resting condition.

Hats Hydraulic Chamber Configuration

Figure 2:
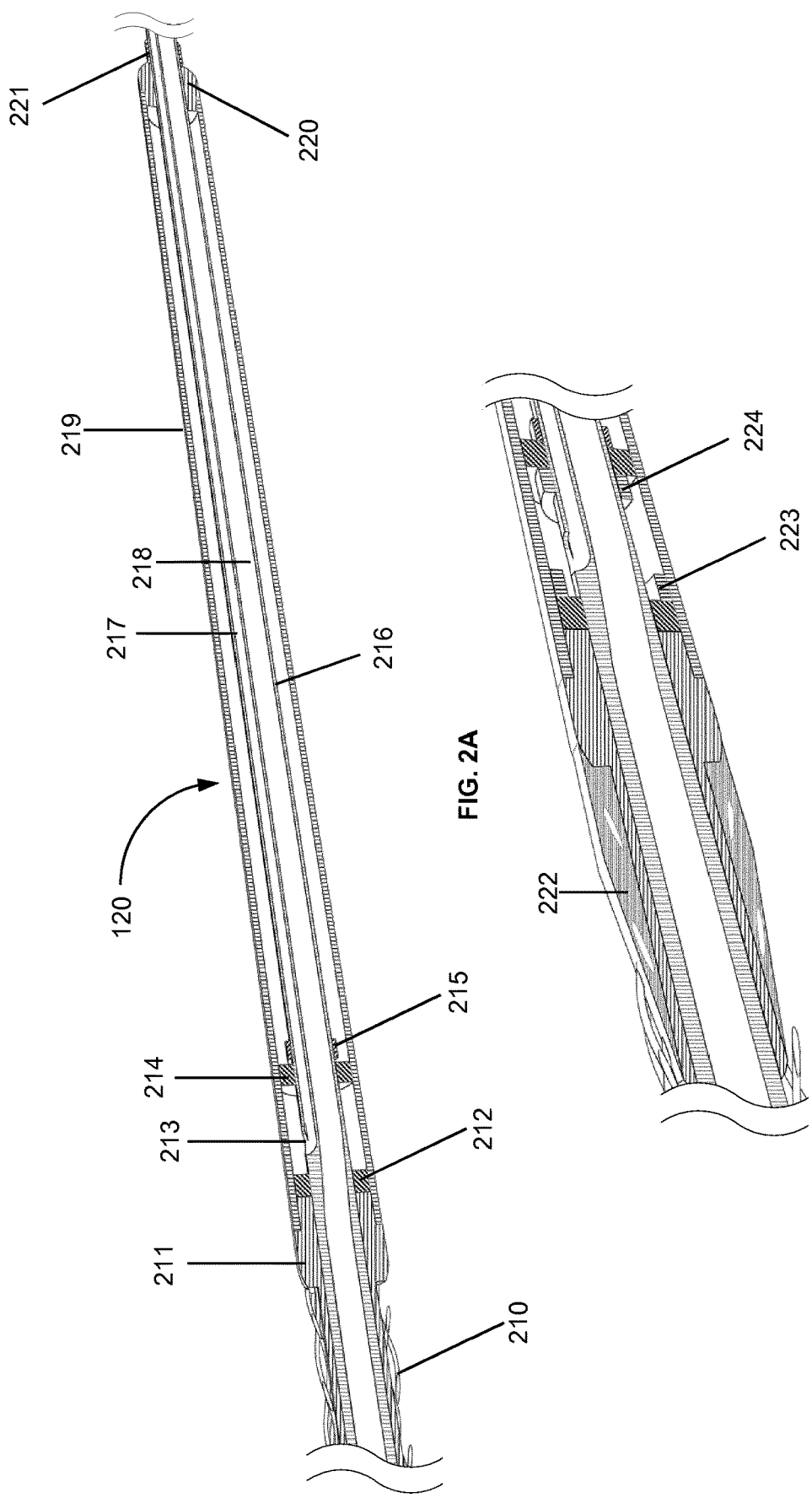
FIG. 2 illustrates a cross-sectional view of a hydraulic braided member propagation mechanism without (FIG. 2A) and with structural reinforcement means (FIG. 2B), as several embodiments.

FIG. 2 illustrates a cross-sectional view of a hydraulic braided member propagation mechanism without (FIG. 2A) and with structural reinforcement means (FIG. 2B), as several embodiments. In FIG. 2A, the hydraulic chamber 120 comprises (from left to right): a distal end plug 211, a distal elastomeric seal/gasket 212, a hydraulic fluid port 213, a proximal elastomeric seal/gasket 214, a distal end stop 215, a dual-lumen configured catheter shaft 216, wherein one lumen is a hydraulic lumen 217, and one lumen is a guide wire lumen 218, an outer tubular member 219, a proximal end plug 220 and a proximal end stop 221. A braided member 210 can be provided fixedly embedded into/adhered onto a portion of the distal end plug, as shown. The hydraulic chamber can be formed between the proximal lateral surface of the distal seal/gasket, the distal lateral surface of the proximal seal/gasket, the internal surface of the outer tubular member, and the external surface of the catheter shaft member coaxially received therein. The distal seal/gasket can extend from the internal surface of the outer tubular member. The proximal seal/gasket can extend from the external surface of the inner tubular member or catheter shaft. The hydraulic chamber is in fluid communication with the hydraulic lumen. Application of hydrostatic pressure exceeding atmospheric pressure can create a force acting on the proximal lateral surface of the annular distal seal in order to propagate the proximal end of the braided member distally, into a substantially compressed configuration. Application of hydrostatic pressure below atmospheric pressure can create a force acting on the proximal lateral surface of the annular distal seal in order to propagate the proximal end of the braided member proximally, into a substantially extended configuration. The maximum axial movement can be defined through the axial boundaries imposed by the respective relative positions of the proximal and distal endstops. The actuation mechanism can be configured for controllable, bi-directional propagation, thereby allowing seamless transition between substantially extended, nominal, and substantially compressed states. FIG. 2B discloses additional structural reinforcement means that can provide enhanced mechanical strength to the sealing surfaces of the hydraulic chamber for optimum device performance under the conditions of repeated bi-directional propagation. In FIG. 2B, the distal and proximal seal can be formed as end face mechanical seal by placement of an annular distal (223) and annular proximal lateral constraint member (224). The distal lateral constraint member can extend from the inner surface of the outer tubular member, whereas the proximal lateral constraint member can extend from the external surface of the inner tubular member or catheter shaft. By utilizing said constraint members, the pressure directly applicable onto each lateral seal surface can be further adjusted based on the constraint member to seal surface area ratio, relieving direct mechanical stress exerted onto the seal. Hence, the structural reinforcement means can provide for additional shear resistance to the sealing surfaces of the distal and proximal seal under the conditions of repeated bidirectional operation, preventing inadverted seal detachment and/or loss of sealing capability. As a related embodiment, a proximal and/or distal portion of the braided member can be provided structurally reinforced by partial embedding with a suitable encapsulant 222. Partial encapsulation of the braided members' proximal and distal end can provide for an alternative attachment means to the distal and proximal end plug, and serve as atraumatic transition to the hydraulic chamber.

Hats Assembly

Figure 3:
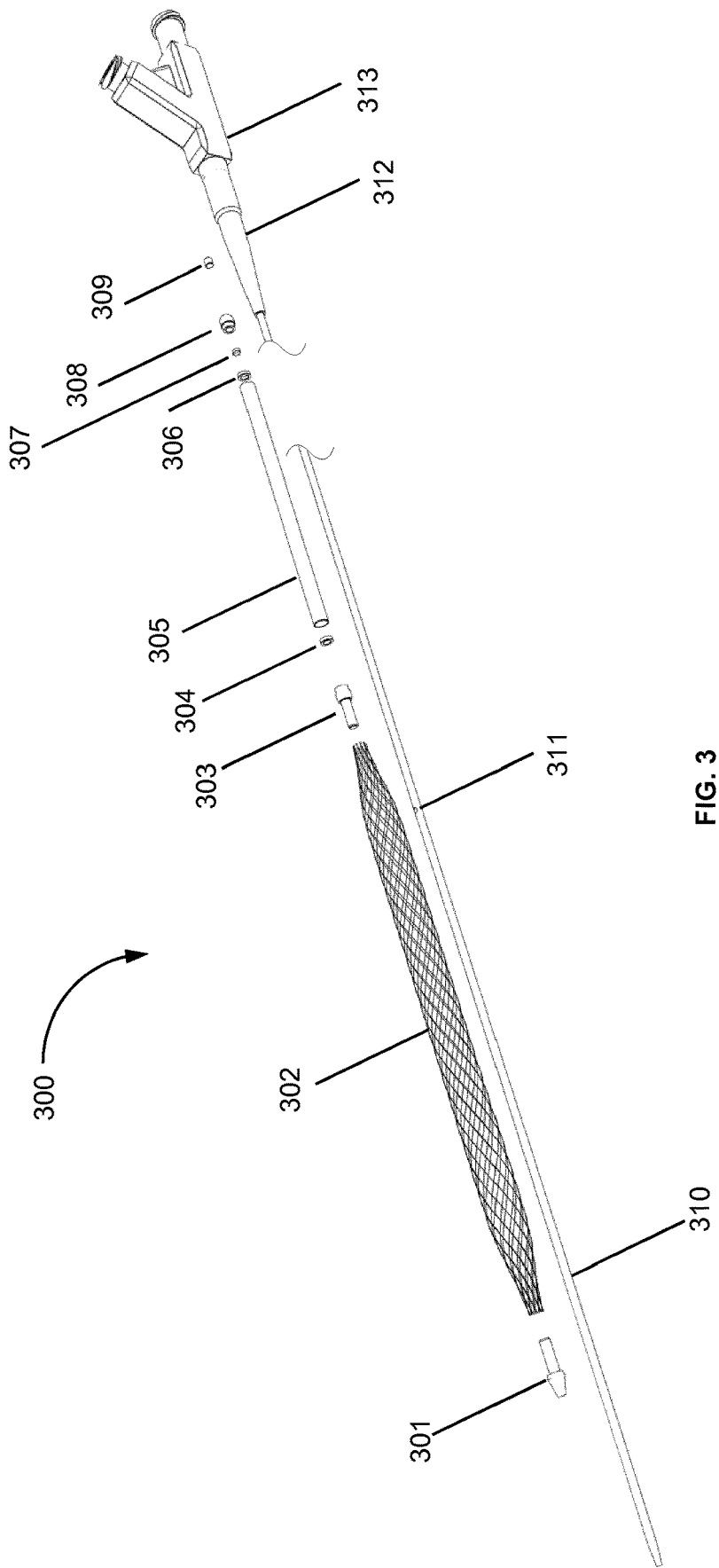
FIG. 3 is a perspective diagram illustrating the assembly components of the HATS catheter system, as an embodiment.

FIG. 3 is a perspective diagram illustrating the assembly components of the HATS catheter system, as an embodiment. In FIG. 3, the catheter assembly 300 comprises (from left to right): a distal catheter tip 301, a braided member 302, a distal end plug 303, a distal seal 304, an outer tubular member 305, a proximal seal 306, a distal end stop 307, a proximal end plug 308, a proximal end stop 309, a catheter shaft 310 including a hydraulic fluid port 311, a kink protector 312 and a manifold 313. The distal catheter tip 301 can be adhered to the distal end of the catheter shaft 310. Components 301-309 can be coaxially aligned over the catheter shaft 310. Components 303-308 can form the sub-assembly components of the hydraulic chamber casing. Components 310, 303 can provide the attachment means for the braided member 302. The braided member can be provided in heat-set form, including shape-memory and/or spring-like properties. As further embodiments, the braid member geometry can further be endowed with an inner, outer or transient, single-, dual- or multiple polymeric liner, fabric or membrane selectively covering one or more distal, proximal and/or lateral regions and/or sections of the open-mesh structure, and combinations thereof. Fixation between components can be facilitated though adhesive-, heat- or mechanical bonding, melt- and solvent glueing, and equivalents. Catheter shaft sections can be formed from a suitable combination of polymeric tubing materials, and provided structurally reinforced. Preferably, shaft construction materials can include aliphatic and aromatic polyamide homoand copolymers, polyether ether ketones, polyacrylates, polycarbonates, and polyurethane polymers and combinations thereof. The sealing components are preferably formed from thermoplastic elastomers, including silicone and ethylene propylene diene monomer derived elastomers.

Hats Actuation Mechanism

Figure 4:
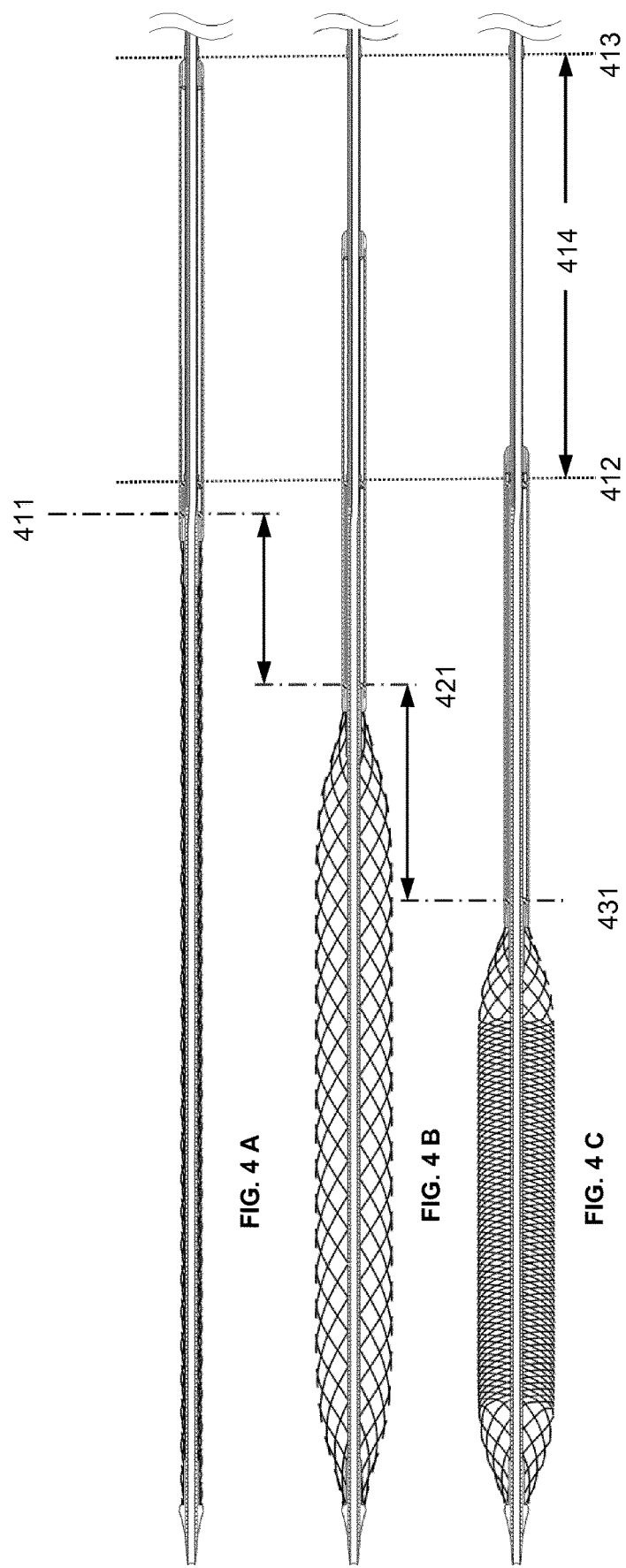
FIG. 4 illustrates a cross-sectional view of a hydraulically actuated, axial braided member propagation mechanism in extended form (FIG. 4A), in nominal/resting form (FIG. 4B), and in compressed form (FIG. 4C), as several embodiments.

FIG. 4 illustrates a cross-sectional view of a hydraulically actuated, axial braided member propagation mechanism in extended form (FIG. 4A), in nominal or resting form (FIG. 4B), and in compressed form (FIG. 4C), as several embodiments. In FIG. 4A-C, the dotted vertical lines 412 and 413 illustrate the fixed axial positions of the proximal and distal end stops during device operation defining an actuation distance 414 of the hydraulic chamber. Dashed vertical lines 411, 421 and 431 illustrate the variable axial positions of the distal elastomeric seal under application of hydrostatic pressure for (A)<1 bar, (B) 1 bar and (C)>1 bar, reflective of extended, nominal and compressed deployment states of the braided member. In order to ensure insertion and maneuvering capability during the pre-deployment stage, the braided member of the HATS catheter system can be applied in a substantially extended configuration, by transferring a negative backpressure (A)<1 bar onto the hydraulic chamber, as described previously. Accordingly, device geometries and dimensions shown in FIGS. 4 A to C, from top to bottom refer to a) a pre-deployment stage in extended configuration, particularly applicable for device insertion, positioning and retrieval; b) a deployment stage at nominal device configuration in absence of an axial load; and c) a deployment state at a substantially compressed device configuration, with an axial load actively maintaining the preset radius of the braided member, particularly applicable for structural vessel support, shielding and/or fixation, dilation, flow diversion and/or filtering, including the capture and extraction of foreign bodies and ablated materials within the braided structure during operation. As further embodiments, the braid member geometry can further be endowed with an inner, outer or transient, single-, dual- or multiple polymeric liner, fabric or membrane selectively covering one or more distal, proximal and/or lateral regions and/or sections of the open-mesh structure, and combinations thereof.

Hats Adaptable For Interconnected Vessels of Differing Diameter

Figure 5:
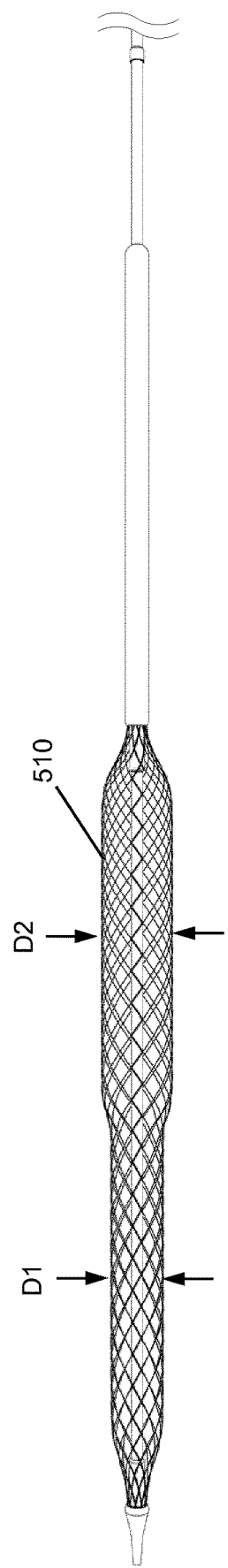
FIG. 5 provides an exemplary braided member design for facilitating therapeutic treatment to interconnected vessels exhibiting two or more diameters, as an embodiment.

FIG. 5 provides an exemplary braided member design for facilitating therapeutic treatment to interconnected vessels exhibiting two or more diameters, as an embodiment. In FIG. 5, a braided mesh structure 510 can be designed with two or more differing diameters D1 and D2, respectively. During manufacturing operations, the braided mesh can be superimposed onto an accordingly shaped mandril geometry, and heat-treated to physically lock the structure into place. As further embodiments, the braid member geometry can further be endowed with an inner, outer or transient, single-, dual- or multiple polymeric liner, fabric or membrane selectively covering one or more distal, proximal and/or lateral regions and/or sections of the open-mesh structure, and combinations thereof. Axial actuation of the braided member structure during deployment can facilitate beneficial adaption to the underlying vascular anatomy with an enhanced radial force, as compared to standard self-expandable stent structures lacking active axial actuation control means. The configuration can be deemed particularly useful for the dilation treatment of stenosed AV fistulas frequently comprising arterio-venous crossover regions with inter-connected vessels of variable size, and generally for provision of therapeutic treatment to bifurcated regions, including the ostium. Treatment options may include the provision of structural vessel support, shielding and/or fixation, dilation, flow diversion and/or filtering capabilities, including the capture and extraction of foreign bodies and ablated materials within interconnected vessels exhibiting two or more diameters.

Hats Adaptable For Non-Uniform Vessels

Figure 6:
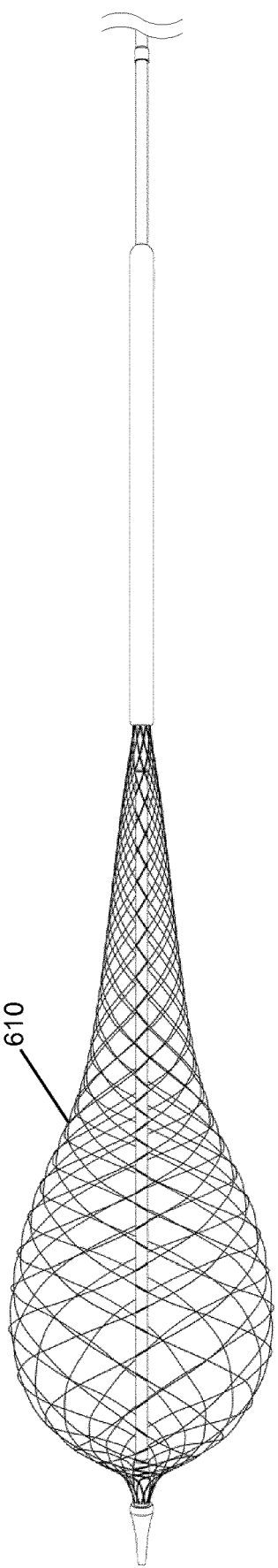
FIG. 6 provides an exemplary braided member design for facilitating therapeutic treatment to non-uniform vessel geometries, as an embodiment.

FIG. 6 provides an exemplary braided member design for facilitating therapeutic treatment to non-uniform vessel geometries, as an embodiment. In FIG. 6, a braided mesh structure 610 can be designed with a continuously varying diameter over the length axis. During manufacturing operations, the braided mesh can be superimposed onto an accordingly shaped mandril geometry, and heat-treated to physically lock the structure into place. As further embodiments, the braid member geometry can further be endowed with an inner, outer or transient, single-, dual- or multiple polymeric liner, fabric or membrane selectively covering one or more distal, proximal and/or lateral regions and/or sections of the open-mesh structure, and combinations thereof. Axial actuation of the braided member structure during deployment can facilitate beneficial adaption to the underlying vascular anatomy with an enhanced radial force, as compared to standard self-expandable stent structures lacking active axial actuation control means. The configuration can be deemed particularly useful for the treatment of terminal aneurysms, and in general, to provide structural vessel support, shielding and/or fixation, dilation, flow diversion and/or filtering capabilities, including the capture and extraction of foreign bodies and ablated materials within non-uniform vessel geometries.

Enhancement of Radial Pressure by Active Hydraulic Axial Device Loading

Figure 7B:
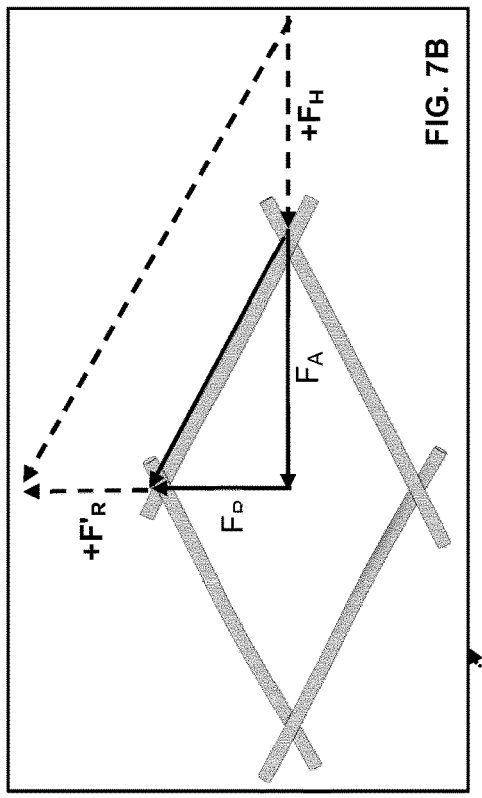
FIG. 7 illustrates two parallelograms of forces of a virtually nominal unit cell of a braided member without (FIG. 7A) versus a unit cell with axial hydraulic load (FIG. 7B) and includes the resulting effect on the schematic hysteresis curves (FIG. 7C), depicting the change of radial force under application of a variable axial hydraulic load, as several embodiments.
Figure 7A:
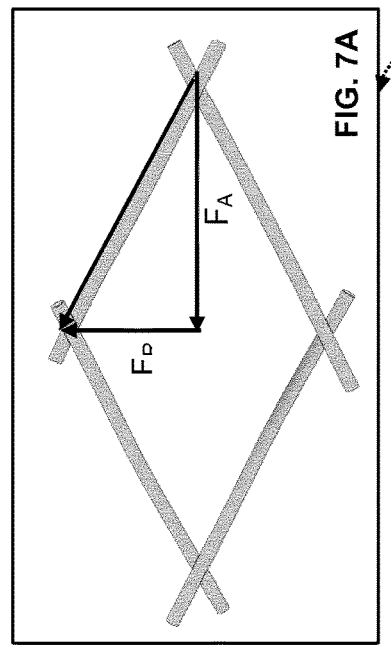
Figure 7C:
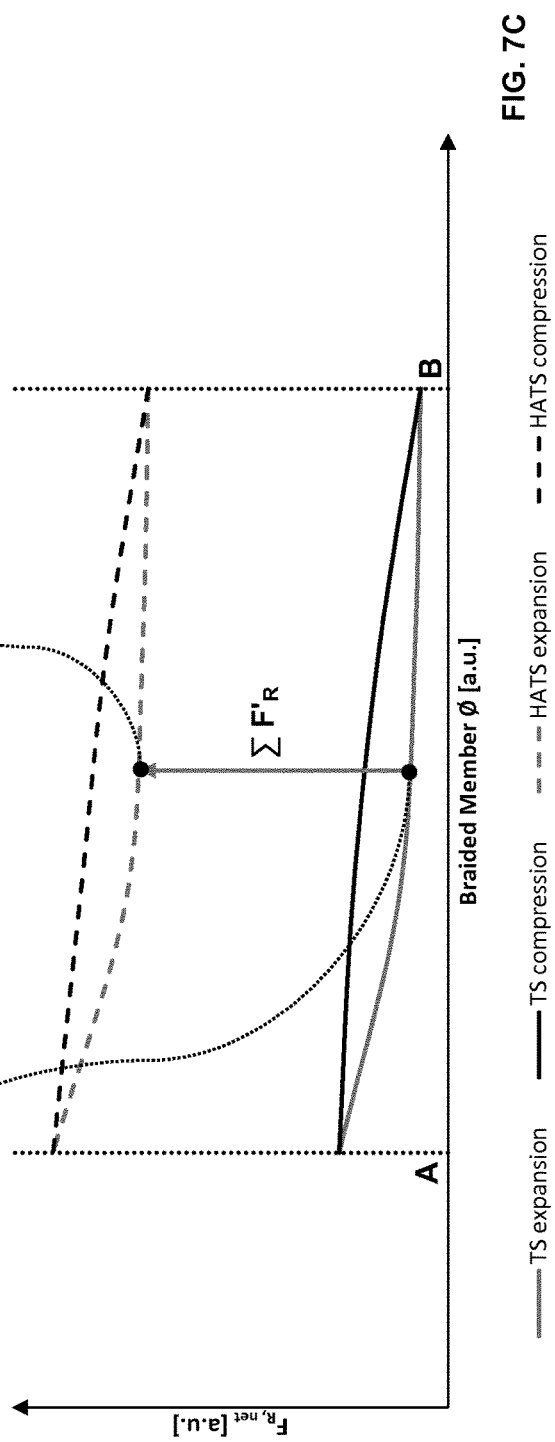

To illustrate the particular benefits of an active axial hydraulic device loading onto a braided member of the present disclosure, the reader is referred to FIG. 7 as a quick and convenient reference. FIG. 7 illustrates two parallelograms of forces of a virtually nominal unit cell of a braided member without (FIG. 7A) versus a unit cell with axial hydraulic load (FIG. 7B), depicting the change of radial force under application of a variable axial hydraulic load, as several embodiments. From left to right, the parallelograms of forces can visualize the vectorial relationship between axial force $F_A$ and radial force $F_R$ in the absence (left insert) and presence of an active axial hydraulic load $F_H$ (right insert). By forming a simple parallelogram of forces it can be shown that the relationship between radial and axial force can be arrived as $$F_R/F_A=(F_R+F'_R)/(F_A+F_H)=F_{R,net}/F_{A,net}$$

thereby implying that upon addition of a hydraulic load $F_H$, the resulting axial force can be increased to $F_{A,net}=F_A+F_H$. At the same time, the resulting radial force can be increased by an additional amount to $F_{R,net}=F_R+F'_R$, so that the above relationship is maintained. In FIG. 7C, the resulting effect on the schematic hysteresis curves on exemplary braided members is shown. In FIG. 7C, the lower pair of solid plotted curves represents a braided members' radial force progression during radial expansion and compression without hydraulic axial actuation (TS=Temporary Scaffold), whereas the upper, dashed plotted pair of curves represents a braided members' radial force progression during radial expansion and compression with hydraulic axial actuation (HATS). The sum of radial force contributions obtained over the braided member's unit cells is depicted as $\Sigma F'_R$ and schematically illustrates the obtained radial force enhancement of the hydraulically actuated braided member. Accordingly, by placing a variably adjustable axial hydraulic load onto the braided member, a variably adjustable amount of additional radial force can be generated, that surpasses the radial force otherwise obtainable from a self-expansive braided member lacking hydraulic axial actuation means. In the following subsections, a more detailed explanation is provided.

A braided members' physical properties, including particularly relevant stress-strain relationships, can be computationally derived by application of the theory of springs, exemplarily referenced in "Mechanical Springs", by A. M. Wahl, Penton Publishing Company, Cleveland, Ohio, 1944. The following relationships have been exemplarily obtained for a nominal, cylindrical braided member geometry (number of braided wires n=12, wire diameter d=0.1 mm, initial braided length $L_0$=40 mm, initial braided mean diameter $D_0$=3.8 mm, initial outer diameter $D_e$=4.0 mm, initial pitch angle $\beta_0$=55°; material=phynox, elastic modulus E=206000 $N/mm^2$, shear modulus G=81500 $N/mm^2$).

Figure 8:
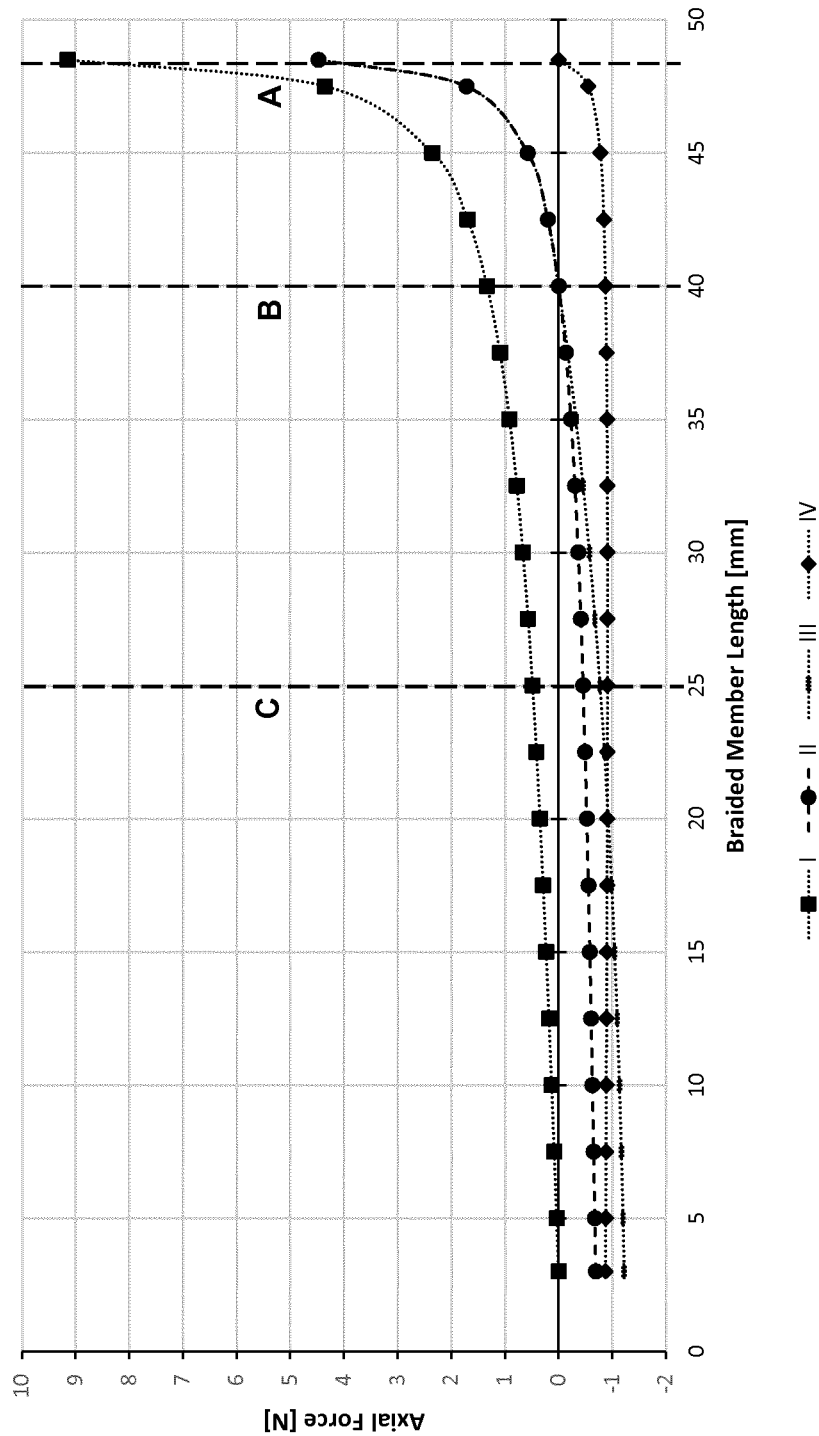
FIG. 8 illustrates change of axial elongation of virtually compressed, nominal and extended braided members under application of variable axial load, as several embodiments.

FIG. 8 illustrates change of axial elongation of virtually compressed, nominal and extended braided members under application of variable axial loads, as several embodiments. In FIG. 8, axial braided member elongation—axial load relationships are presented for four individual cases I-IV, as follows:

Case I: Virtual extension of a maximally compressed braided member (Solid Height $L_S$=3.0 mm, pitch angle $\beta_S$=3.5°) to a maximally extended length (L=48.5 mm, and outer diameter $D_e$=0.97 mm), heat-set in maximal axial compression state.

Case II: Virtual extension/compression of a nominal braided member (Length $L_0$=40.0 mm, outer diameter $D_e$=4.0 mm and pitch angle $\beta_0$=55°) between aforementioned maximally compressed and extended lengths, heat-set in nominal state.

Case III: Virtual extension/compression of a nominal braided member (Length $L_0$=40.0 mm, outer diameter $D_e$=4.0 mm and pitch angle $\beta_0$=55°) between aforementioned maximally compressed and extended lengths, heat-set in nominal state under consideration of a lateral constraint (e.g. placement in a vessel, $D_e \leq 4.0$ mm).

Case IV: Virtual extension of a maximally extended braided member ((L=48.5 mm, and outer diameter $D_e$=0.97 mm) to a maximally compressed length (Solid Height $L_S$=3.0 mm, pitch angle $\beta_0$=3.5°), heat-set in maximal axial extension state.

Cases I and IV can represent braided members heat-set in considerably minimum and maximum axial elongation states useful for prediction of maximum virtual work of axial extension and compression. Cases II and III can represent braided members heat-set at a nominal (design specification) state useful for the prediction of variable amounts of virtual work of axial extension and/or compression. A nominal state selected from an interim state between minimum and maximum axially extended state can represent a preferred embodiment of the underlying disclosure. Dashed vertical lines indexed with capital letters A, B, and C reference back to the device geometries presented in FIG. 4, to denote a substantially extended (see FIG. 4A), a nominal or resting form (see FIG. 4B), and a substantially compressed form (see FIG. 4C).

The area under each of the curve I-IV can be reflective of the virtual work of axial deformation required to deform the given braided member within the boundary conditions imposed by the respective example cases. Positive amounts of axial forces represent a tensile force, and negative axial forces represent a compressive force. Accordingly, case I can require a positive net amount of work, equivalent to a positive tensile force applied over the specified extension distance, to fully extend the pre-set braided member from fully compressed (C) to fully extended condition (A). Vice versa, case IV can require a negative net amount of work, equivalent to a compressive force applied over the specified compression distance, to fully compress the pre-set braided member from fully extended (A) to fully compressed condition (C). At the time point of manufacture, heat-setting each braided member at the specified dimensional (L, D, β) starting point can relieve the respective braided members from the respective intrinsic compressive or tensile energy stored inside the braided mesh structure, thereby allowing to precisely predetermine whether the axial load required to effect a desired deformation is of positive or negative, respectively tensile or compressive nature. Case II and III represent laterally unconstrained and laterally constrained braided member geometries heat-set at the desired nominal or design specification. In both of these cases, a positive net amount of work, equivalent to a positive, or tensile force applied over a specified extension distance, can be required to extend the pre-set braided member geometry from nominal (B) to extended condition (A), and a negative net amount of work, equivalent to a compressive force applied over a specified compression distance, to compress the pre-set braided member from nominal (B) to compressed condition (C). Upon removal of the respective axial load and/or lateral constraints, the braided member is capable of releasing the compressive or tensile energy temporarily stored in the mesh structure, returning to the nominal state geometry (B). The described behavior in heat-set state can be reflective of shape-memory or spring-like properties.

Figure 9:
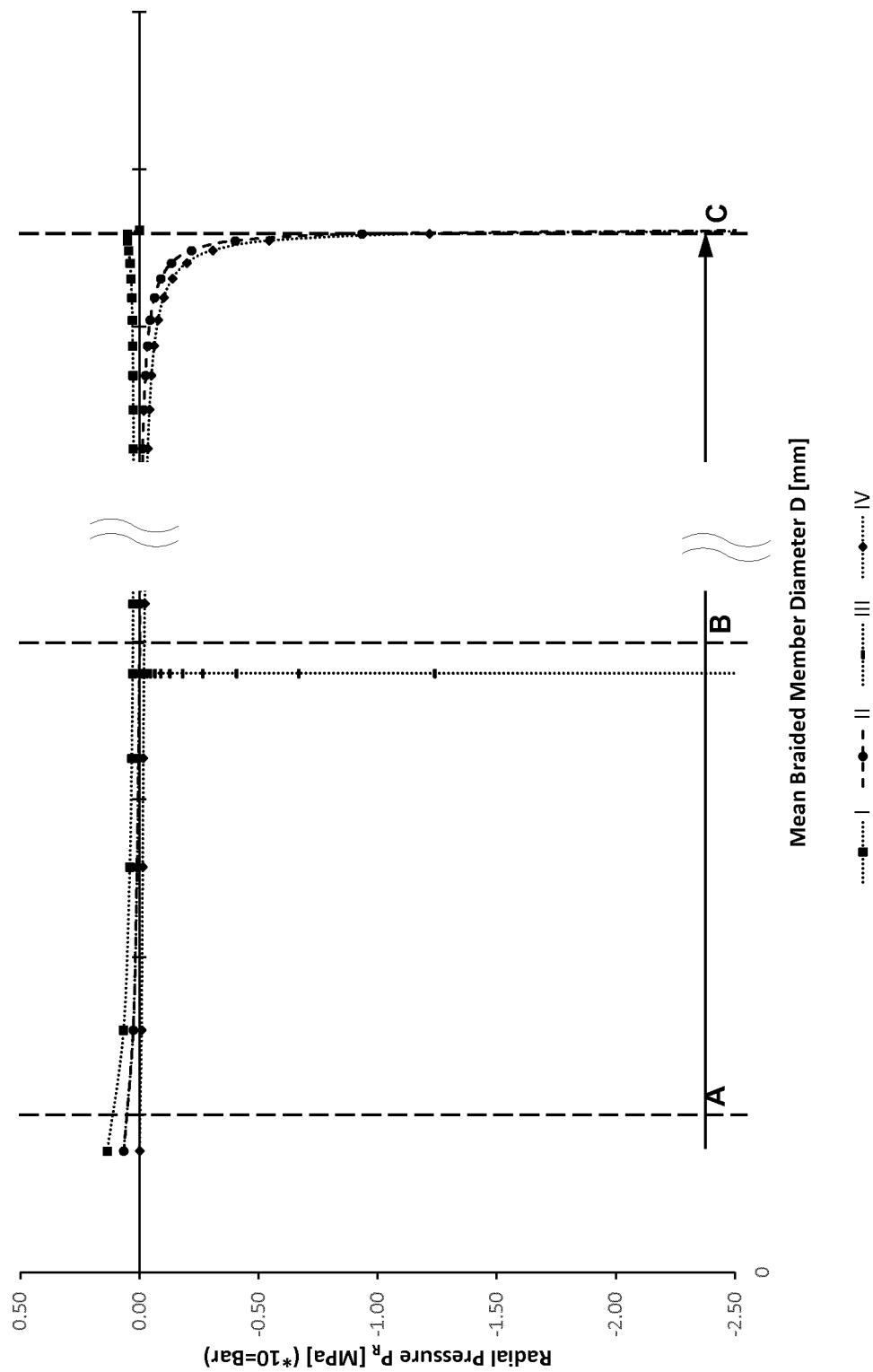
FIG. 9 illustrates change of radial elongation of virtually compressed, nominal and extended braided members under application of variable radial pressure, as several embodiments.

FIG. 9 illustrates change of radial elongation of virtually compressed, nominal and extended braided members under application of variable radial pressure, as several embodiments. In FIG. 9, several braided member radial elongation—radial pressure relationships are examined for the four individual cases I-IV previously described in FIG. 8. While radial and axial deformation can occur substantially at the same time, the terms extension, expansion and compression as specifically used in this example refer to the radial components of deformation, unless indicated otherwise.

Cases I and IV can represent braided members heat-set in considerably maximum and minimum radial elongation states useful for prediction of maximum virtual work of radial compression and extension. Cases II and III can represent braided members heat-set at a nominal (design specification) state useful for the prediction of variable amounts of virtual work of radial compression and/or extension. A nominal state selected from an interim state between minimum and maximum radially extended state can represent a preferred embodiment of the underlying disclosure. Dashed vertical lines indexed with capital letters A, B, and C reference back to the device geometries presented in FIG. 4, to denote a substantially extended (see FIG. 4A), a nominal or resting form (see FIG. 4B), and a substantially compressed form (see FIG. 4C).

The area under each of the curves I-IV can be reflective of the virtual work of radial deformation required to deform the given braided member within the boundary conditions imposed on the respective example cases I-IV. Positive amounts of radial pressure represent a virtual compressive or radial force acting inward on the substantially cylindrical braided surface area, and negative amounts of radial pressure represent a virtual expansive or radial force acting outward from the substantially cylindrical braided surface area. In analogy to the axial deformation relationships presented in FIG.8, case I can require a positive net amount of work, equivalent to a positive radially compressive force applied over a specified radial distance, to fully radially compress the pre-set braided member from the diameter obtainable at solid height $L_s$ (C) to the diameter present at fully extended length (L=48.5 mm, $D_e$=0.97 mm) (A). Vice versa, case IV can require a negative net amount of work, equivalent to a radially expansive force applied over the specified compression distance, to radially expand the pre-set braided member from a fully compressed (A) to fully expanded condition (C). At the time point of manufacture, heat-setting each braided member at the specified dimensional (L, D, β) starting point can relieve the respective braided members from the respective intrinsic compressive or expansive energy stored inside the braided mesh structure, thereby allowing to precisely predetermine whether the desired radial deformation properties can be effected by positive or negative, respectively inward or outward acting radial force contributions. Case II and III represent laterally unconstrained and laterally constrained braided member geometries heat-set at the desired nominal or design specification. In both of these cases, a positive net amount of work, equivalent to a positive radially compressive force applied over a specified radial distance can be required to radially compress the pre-set braided member geometry from nominal (B) to fully compressed condition (A), and a negative net amount of work, equivalent to an expansive force applied over a specified radial distance, to expand the pre-set braided member from nominal (B) to fully expanded condition (C). Upon removal of the respective radial load and/or lateral constraints, the braided member is capable of releasing the compression or expansion energy temporarily stored in the mesh structure, returning to the nominal state geometry.

Through the considerations provided in FIGS. 7-9, it can be accordingly derived, that by placement of a compressive axial load onto a braided member heat-set at nominal dimensions (as referenced through example cases II and III) an outward acting radial force can be generated. In the absence of an axial load, the radial force of an unconstrained braided member at nominal state is zero. By utilizing a hydraulic actuation mechanism, a well-definable axial load can be controllably placed onto the braided member, resulting in a substantially increased radial force available for enhanced treatment of desired target vessel anatomies. In the presented example case III, the radial pressure generated at a target vessel diameter of about 4 mm can be predictably estimated to exceed a range of 20-25 bars, which is on the same order of magnitude as compared to contemporary dilation balloons.

Adaptation of Hats Mesh Size and Lateral Device Permeability

Figure 10:
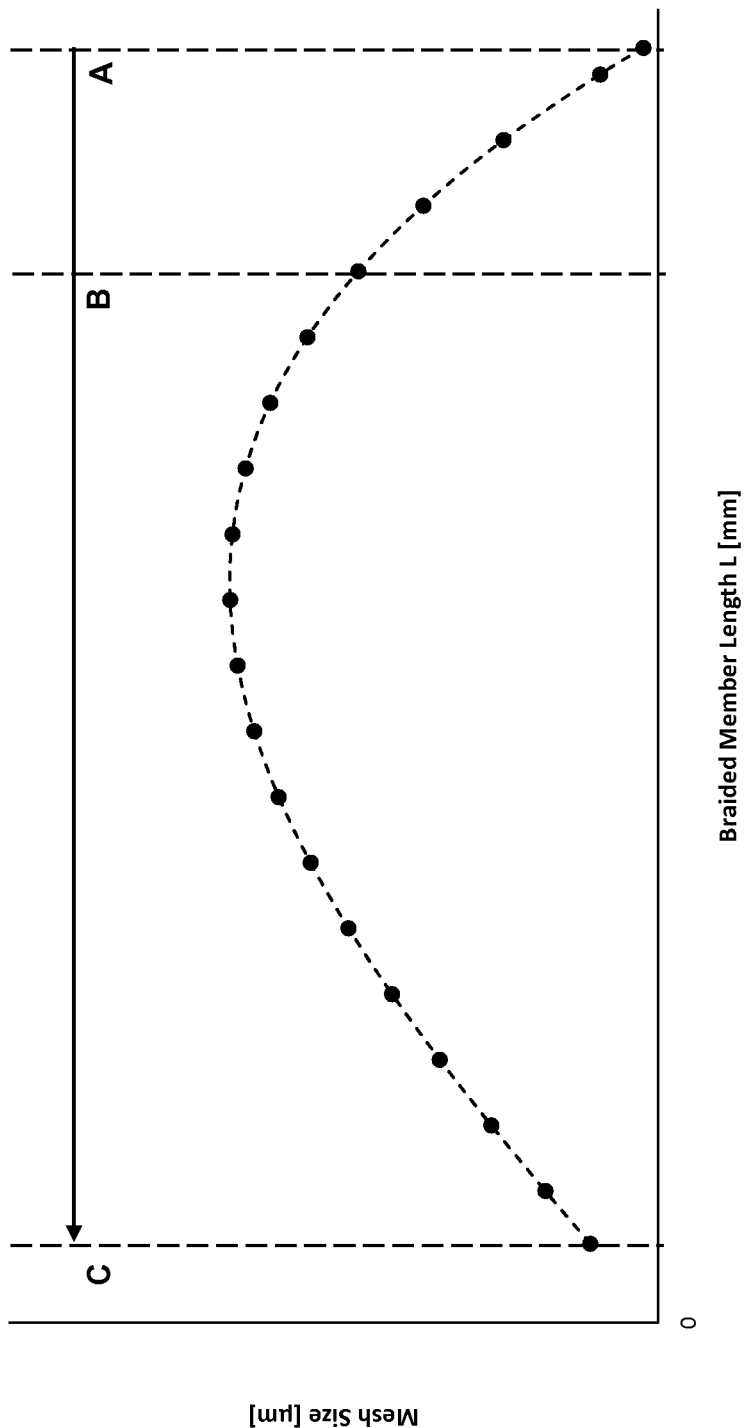
FIG. 10 illustrates change of mesh size of a virtually nominal braided member at variable degrees of axial extension, as an embodiment.

FIG. 10 illustrates change of mesh size of a virtually nominal braided member at variable degrees of axial extension, as an embodiment. In FIG. 10, the plot can be derived from the example braided geometry of case II as described in FIGS. 8-9. Dashed vertical lines indexed with capital letters A, B, and C reference back to the device geometries presented in FIG. 4, to denote a substantially extended (see FIG. 4A), a nominal or resting form (see FIG. 4B), and a substantially compressed form (see FIG. 4C). Starting from the device geometry in a substantially extended form A (as indicated through the arrow), at a first minimum mesh size of the braided member, the mesh size can continually increase, passing through device geometry in nominal form B, until it can reach a maximum value further definable through device dimensional parameters. Upon further axial compression towards device geometry C, the mesh size can approach a second, smaller mesh size that can become fully minimized at solid height. Depending on the initial pitch angle of the provided braided member structure, the respective mesh size maxima and minima can be further adjusted as desired. The braided member calculation is provided in a virtually unconstrained form. Lateral constraints, including physical wire entanglement, friction between wires, and presence of axial and radial barriers (e.g. end stops of the hydraulic chamber, vessel wall) can further limit the obtainable magnitude of axial and radial deflection, and accordingly, mesh size. Mesh size, as disclosed herein, refers to the in-circle diameter of the rhomboid- or diamond-shaped unit cell of a braided member.

Adaptation of Hats Surface Coverage

Figure 11:
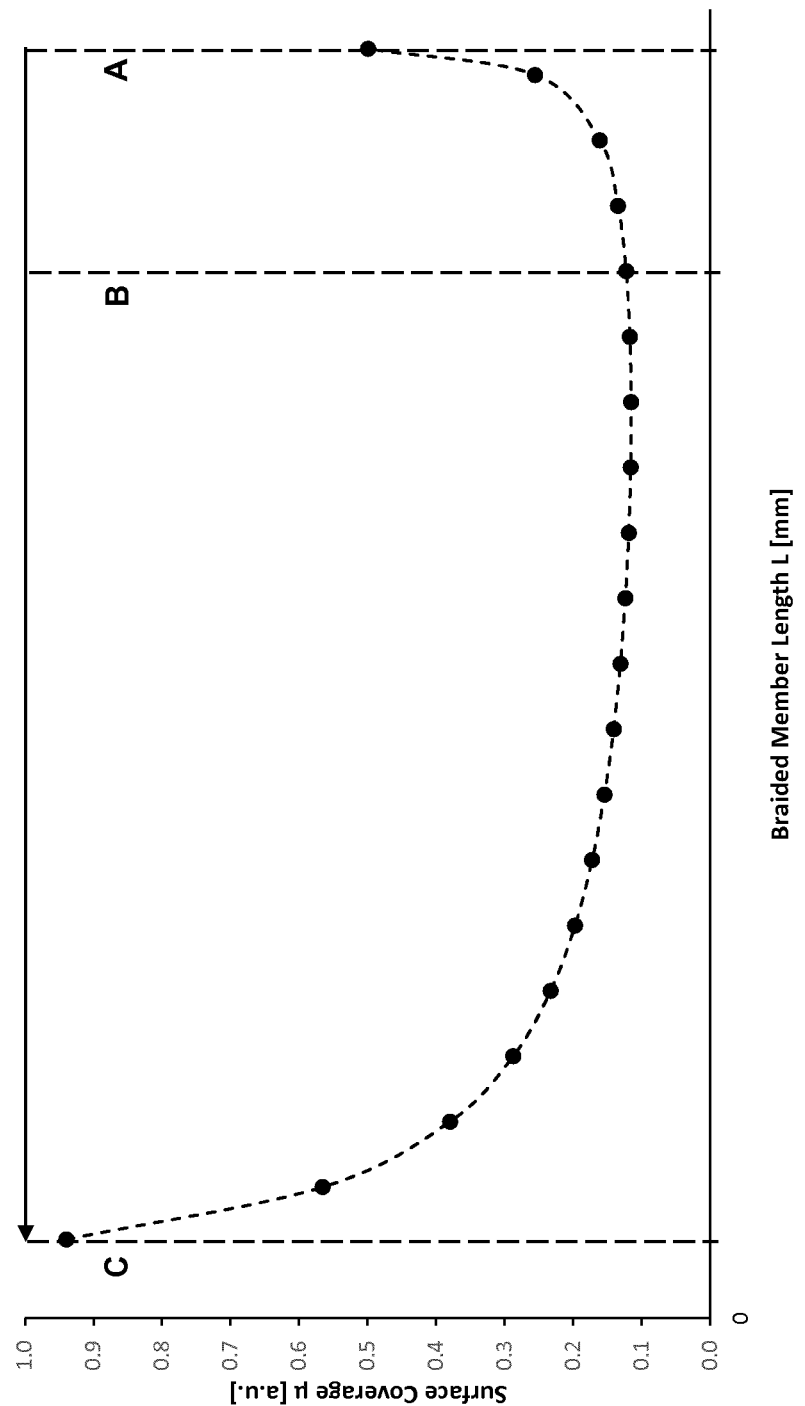
FIG. 11 illustrates change of surface coverage of a virtually nominal braided member at variable degrees of axial extension, as an embodiment.

FIG. 11 illustrates change of surface coverage of a virtually nominal braided member at variable degrees of axial extension, as an embodiment. In FIG. 11, the surface coverage can be derived from the example braided geometry of case II as described in FIGS. 8-9, and defined as the ratio between the braided wire surface area and the virtual cylinder surface area of the braided member, to serve as a convenient criterion defining mesh density at any given axial extension. Dashed vertical lines indexed with capital letters A, B, and C reference back to the device geometries presented in FIG. 4, to denote a substantially extended (see FIG. 4A), a nominal or resting form (see FIG. 4B), and a substantially compressed form (see FIG. 4C). Starting from the device geometry in a substantially extended form, at a first maximum surface coverage of the braided member, the surface coverage can continually decrease, passing through device geometry in nominal form B, until it can reach a minimum value further definable through device dimensional parameters. Upon further axial compression towards device geometry C, the surface coverage can approach a second, greater surface coverage that can become fully maximized at solid height. The braided member calculation is provided in a virtually unconstrained form. Lateral constraints, including physical wire entanglement, friction between wires, and presence of axial and radial barriers (e.g. end stops of the hydraulic chamber, vessel walls) can further limit the obtainable magnitude of axial and radial deflection, and accordingly, surface coverage.

Adaptation of Hats Device Dimensions

Figure 12:
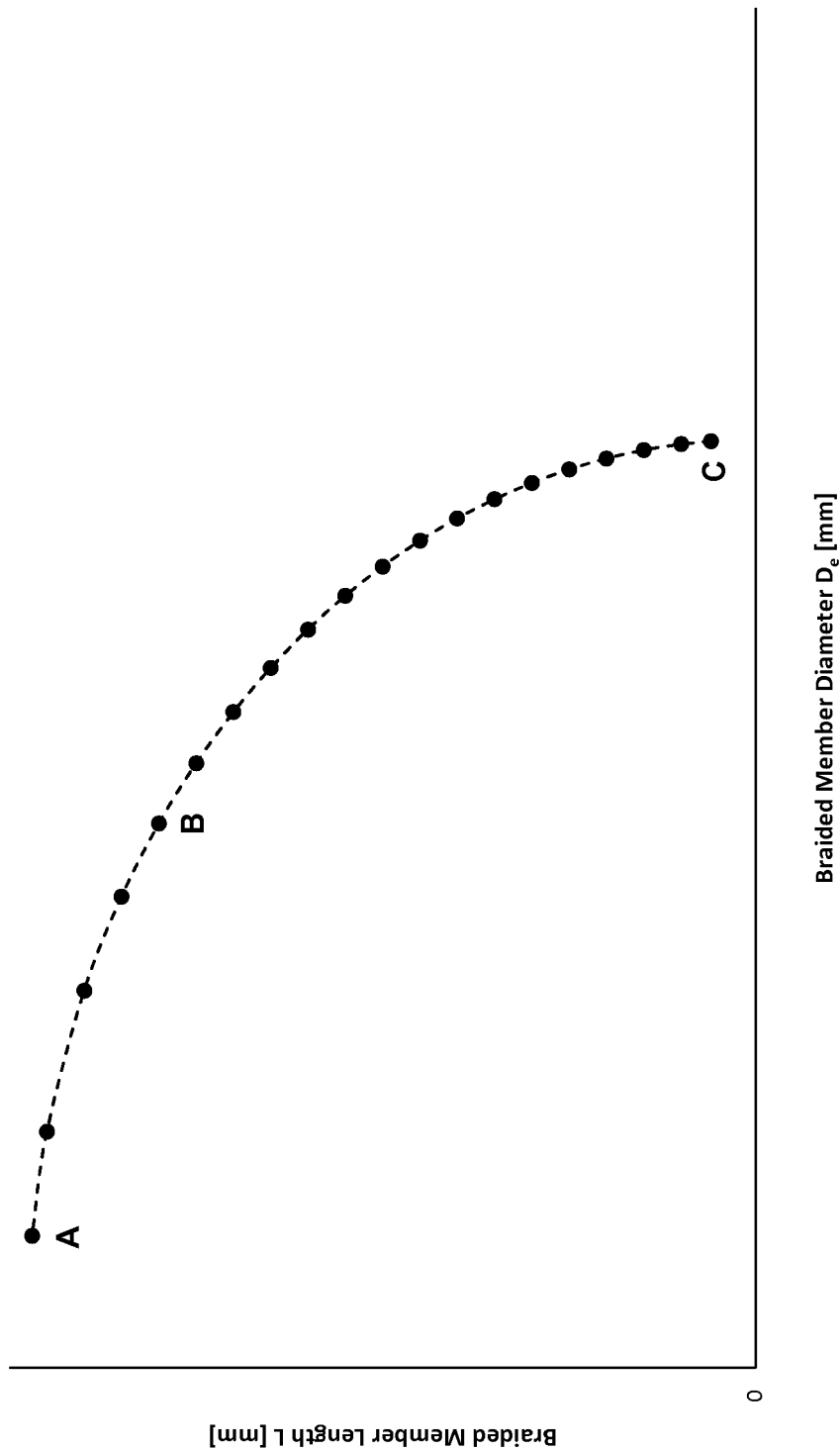
FIG. 12 illustrates the progression between minimum and maximum radial elongation states of a virtually nominal braided member at variable degrees of axial extension, and vice versa, as an embodiment.

FIG. 12 illustrates the progression between minimum and maximum radial elongation states of a virtually nominal braided member at variable degrees of axial extension, and vice versa, as an embodiment. In FIG. 12, a dimensional state diagram (Length L, Diameter D) of the braided structure previously described as case II of FIGS. 8-9 is provided. Capital letters A, B, and C reference back to the device geometries presented in FIG. 4, to denote a substantially extended (see FIG. 4A), a nominal or resting form (see FIG. 4B), and a substantially compressed form (see FIG. 4C). The diagram can conveniently describe the dimensional relationship between simultaneous axial and radial deformation of a braided member under application of a given load. Therefore, the radial extension of a braided member at any given axial extension, and vice versa can be effectively predicted. The braided member calculation is provided in a virtually unconstrained form. Lateral constraints, including physical wire entanglement, friction between wires, and presence of axial and radial barriers (e.g. end stops of the hydraulic chamber, vessel wall) can further limit the obtainable magnitude of axial and radial deflection.

Vessel Dilatation and Vessel Wall Repair

Figure 13:
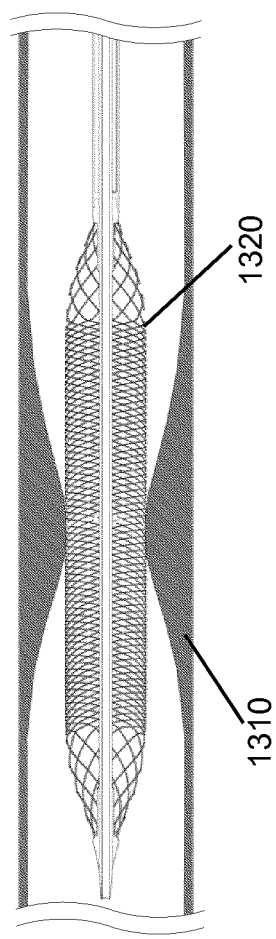
FIG. 13 illustrates a cross-sectional view of a hydraulically actuated braided member of FIG. 1, positioned in a target vessel anatomy to facilitate treatment, as an embodiment.

FIG. 13 illustrates a cross-sectional view of a hydraulically actuated braided member of FIG.1, positioned in a target vessel anatomy to facilitate treatment, as an embodiment. In FIG. 13, a cross-sectional diagram of a portion of a patients' vascular system is shown. The distal working end portion of the HATS catheter system, comprising a hydraulically actuatable braided member 1320, has been adequately positioned in the center of a lesion 1310 by angiographic control means. Through exertion of a well-definable axial hydraulic load on the braided member, the braided structure can be forced into the target lesion, with a much enhanced radial force, thereby providing a more efficient form of lesion treatment as compared to a self-expandable stent member. Sometimes, during the process of an interventional procedure, patches of vascular layers forming the lumen of a vessel can dislodge, resulting in flaps that can protrude intraluminally and disrupt blood flow. In such cases, the catheter system of the present disclosure can also be deployed to press the flap back against the vessel wall, effectively repairing the defective region of the vessel.

Figure 14:
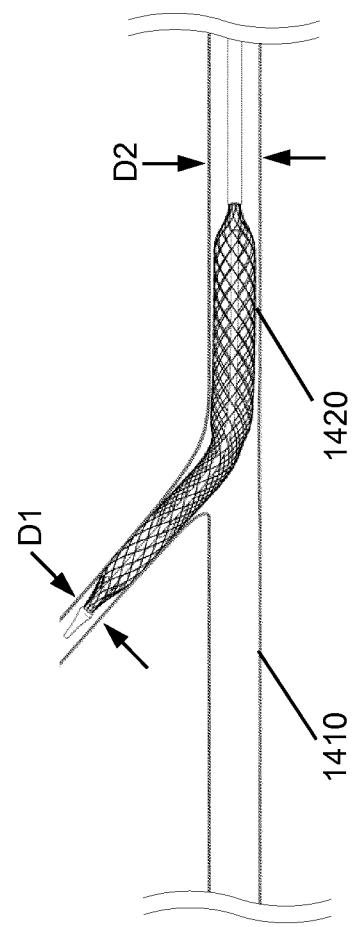
FIG. 14 illustrates a cross-sectional view of a hydraulically actuated braided member of FIG. 5, positioned in a target vessel anatomy to facilitate treatment, as an embodiment.

Vessel Dilation, Flow Diversion, Vessel Wall Support and Stabilization Through Variable Contour Adaptation FIG. 14 illustrates a cross-sectional view of a hydraulically actuated braided member of FIG. 5, positioned in a target vessel anatomy to facilitate treatment, as an embodiment. In FIG. 14, a cross-sectional diagram of a portion of a patients' vascular system is shown. The distal working end portion of the HATS catheter system, comprising a hydraulically actuatable braided member 1420, has been adequately positioned in a bifurcated region 1410 exhibiting dissimilar vessel diameters, for example a arteriovenous crossover region within an AV fistula. Through application of an axial load, the dual-diameter braided mesh can be safely anchored into the bifurcated region without risk of overextending each respective vessel. Further still, in the presence of a lesion, including hardened and /or calcified tissue, the axially-loaded braided structure can be applied with a much enhanced radial force to effectively restore luminal patency during deployment as compared to a self-expandable stent member.

Figure 15:
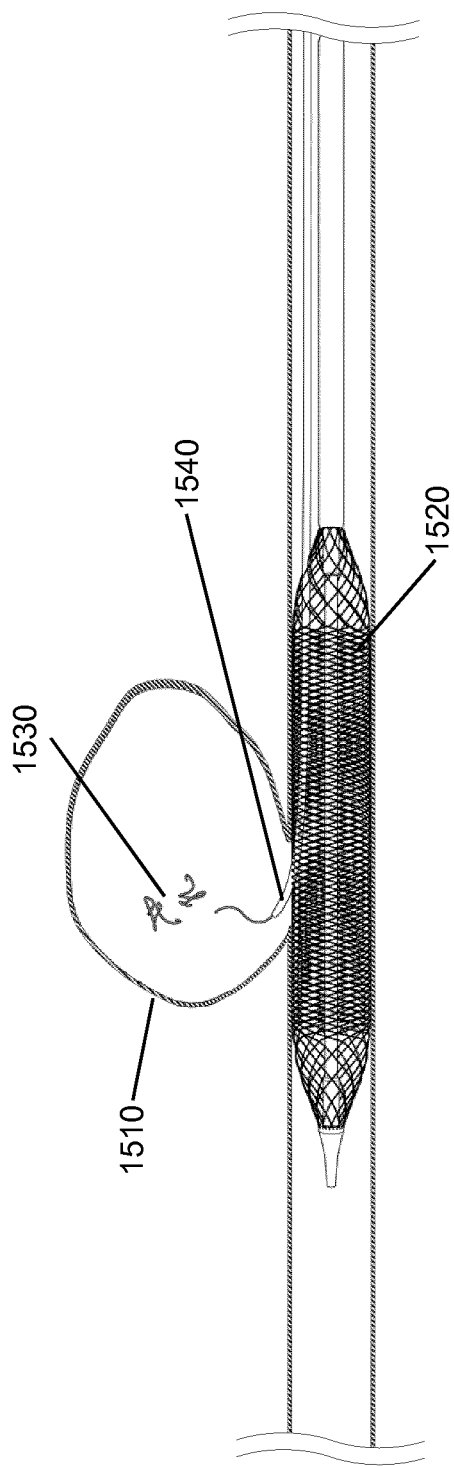
FIG. 15 illustrates a cross-sectional view of a hydraulically actuated braided member of FIG. 1, positioned in a target vessel anatomy to facilitate treatment, as an embodiment.

Flow Diversion, Hemostasis, Aneurysm Coiling Assist, Embolic Protection, Foreign Body Capture and Retrieval FIG. 15 illustrates a cross-sectional view of a hydraulically actuated braided member of FIG. 1, positioned in a target vessel anatomy to facilitate treatment, as an embodiment. In FIG. 15, a cross-sectional diagram of a portion of a patients' vascular system is shown. The distal working end portion of the HATS catheter system, comprising a hydraulically actuatable braided member 1520, can be adequately positioned in the vessel lumen adjacent to a wide-necked aneurysm 1510. Consecutively, a microcatheter 1540 intended for aneurysm embolization can be advanced through or around the temporarily expanded braided member, so that the distal tip of the microcatheter can enter the aneurysm sac. Prior to the release of coils 1530, the mesh size of the braided member can be controllably decreased through hydraulic axial actuation of the braided member, such that the micro-catheter inserted through the lateral wire mesh of the braided member can be actively stabilized, preventing inadverted loss of position. In case of a side by side placement above the lateral braided surface, the controllably adjustable axial actuation means of the braided member can be utilized to achieve an atraumatic, dimensional and radial force adaption, resulting in a similarly stabilizing effect. In addition, the radial pressure exerted through the braided member can further stabilize the vessel lumen, while the decreased mesh size on the lateral braided surface can effectively prevent stray coils from entering the vessel lumen. During the procedure, the flow of blood to the aneurysm sac can be controllably diverted as a function of the underlying mesh size. Given a certain degree of axial compression, the mesh size reduction can be sufficient to disrupt the flow of blood to the aneurysm to such a degree, that the blood contained within the aneurysm can coagulate. In comparison, the cone regions of the braided member can remain substantially open, thereby adequately maintaining the blood flow within the vessel lumen. Further still, the braided mesh can be capable of capturing thrombotic masses, ablated materials and/or foreign bodies, such as aforementioned coils, within the braided structure during operation. Upon reversal of the axial compression, these materials can stay entrapped within the braided structure, facilitating convenient retrieval from the treatment side.

Figure 16:
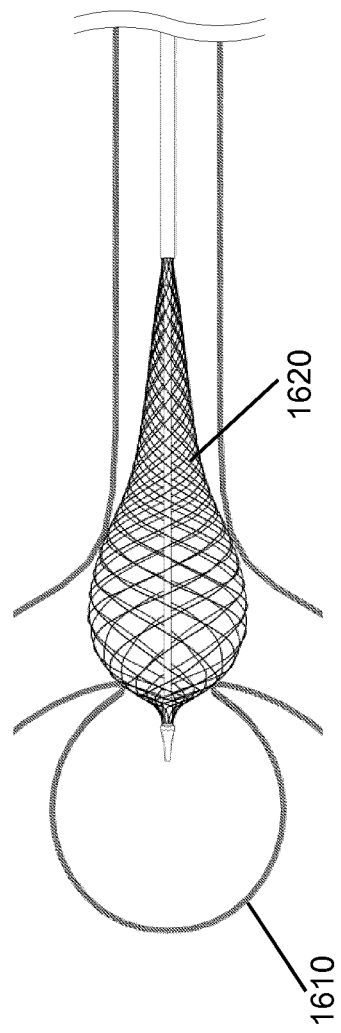
FIG. 16 illustrates a cross-sectional view of a hydraulically actuated braided member of FIG. 6, positioned in a target vessel anatomy to facilitate treatment, as an embodiment.

Vessel Wall Support and Stabilization Through Variable Contour Adaptation, Flow Diversion FIG. 16 illustrates a cross-sectional view of a hydraulically actuated braided member of FIG. 6, positioned in a target vessel anatomy to facilitate treatment, as an embodiment. In FIG. 16, a cross-sectional diagram of a portion of a patients' vascular system is shown. The distal working end portion of the HATS catheter system, comprising a hydraulically actuatable braided member 1620, can be adequately positioned in a trifurcated region, for example the main vessel lumen adjacent to a terminal aneurysm 1610. By provision of an axial load, the nominal braided member geometry can be favorably expanded to adapt to the variable vessel contour as shown, and anchored with an enhanced radial force, to provide needed support. Upon anchoring, the braided member can further be used for aneurysm embolization, having the same or similar benefits as previously described for the alternate braided member geometry of FIG. 15.

Aneurysm Closure Device

Figure 17:
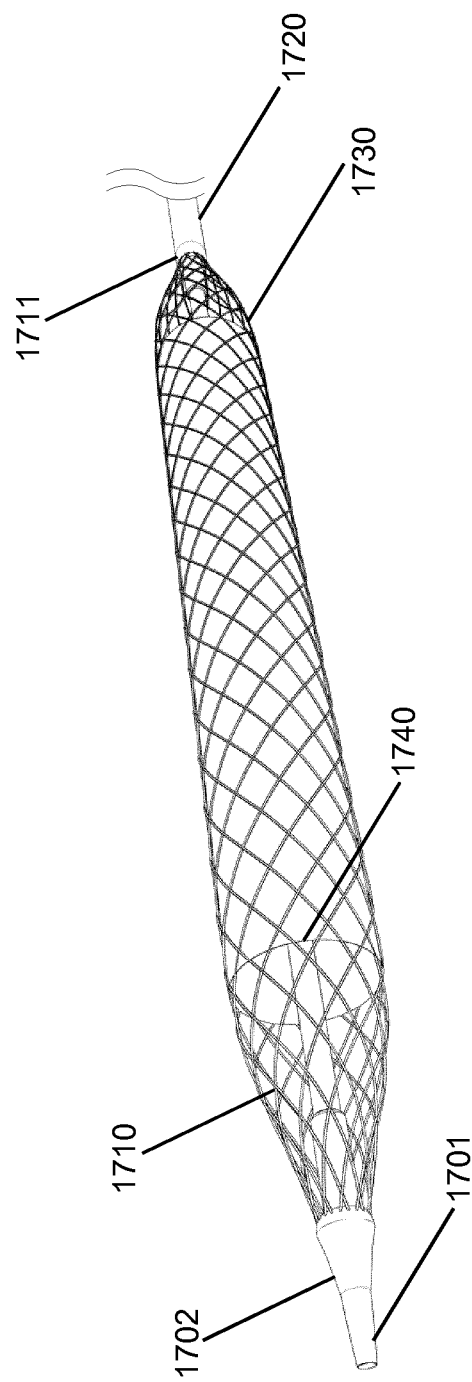
FIG. 17 provides an exemplary braided member design in a deployed state, for performing aneurysm and/or vessel closure, as an embodiment.

FIG. 17 provides an exemplary braided member design in a deployed state, for performing aneurysm and/or vessel closure, as an embodiment. In FIG. 17, the hydraulically actuatable braided member structure 1710 located between a distal end plug 1702 and a proximal end plug 1711 is adhered to the hydraulic chamber casing 1720 and coaxially aligned over a distal catheter shaft portion having a catheter tip 1701. The braided member structure can be derived from the braided member structure as disclosed in FIG. 4, and additionally comprises a micro- and/or macroporous polymeric membrane 1740. The membrane can be utilized for decreasing lateral blood permeability from a vessel lumen to an aneurysm sac during deployment, such that lateral blood flow to the aneurysm is substantially impeded, effecting blood coagulation within the cavity and shielding the lumen from embolic events at substantially the same time. Other suitable applications include the closing of ruptured vessels as a bailout device. Axial actuation of the braided member structure during deployment can facilitate beneficial adaption to the underlying vascular anatomy with both controllable amount of radial force and dimensions, further improving both lateral sealing and vessel anchoring capability. By combining the variable permeability characteristics of the hydraulically actuatable braid member with the intrinsic permeability properties of a polymeric membrane, the braid can be constructed with a lesser number of wire pairs as compared to a non-covered braided member, thereby maintaining an at least comparable or superior lateral sealing and shielding capability in a deployed state. Additional benefits may include decreased crossing profile and improved flexibility of the braided member.

Embolic Protection Device

Figure 18:
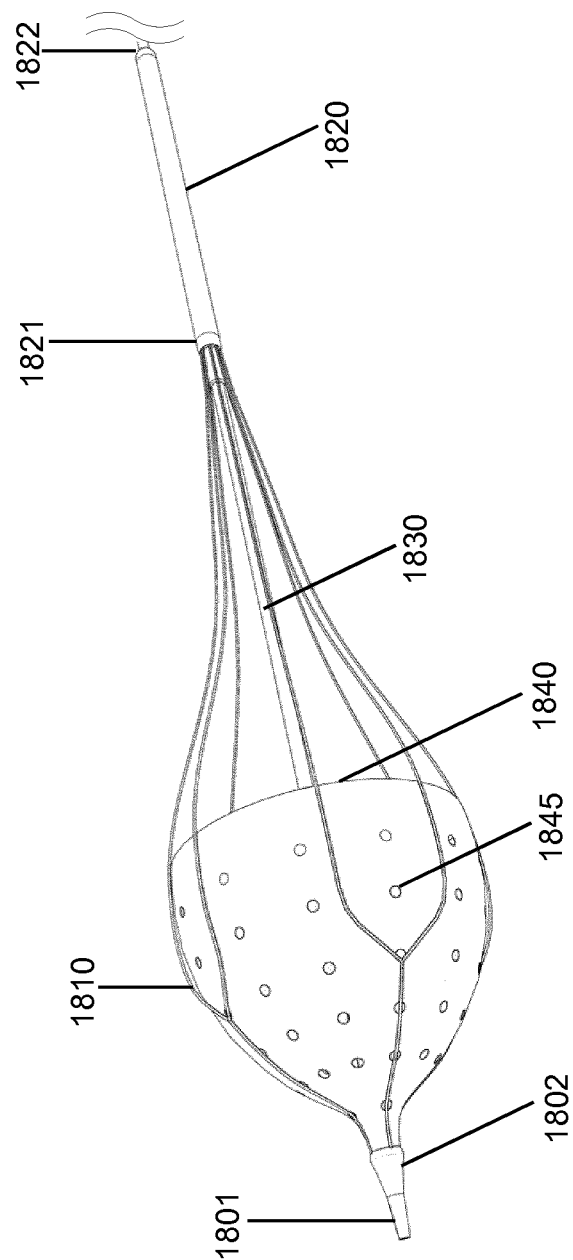
FIG. 18 illustrates an exemplary wire scaffold design in a deployed state, for facilitating embolic protection, as an embodiment.

FIG. 18 illustrates an exemplary wire scaffold design in a deployed state, for facilitating embolic protection, as an embodiment. In FIG. 18, the hydraulically actuatable wire scaffold 1810 located between a distal end plug 1802 and a proximal end plug 1821 is adhered to the hydraulic chamber casing 1820 and coaxially aligned over a distal catheter shaft portion having a catheter tip 1801. The wire scaffold exhibits a varying diameter across a length section, similar to the braided member structure disclosed in FIG. 6, and additionally comprises a polymeric membrane 1840 interspersed with macroscopic pores 1845 in the sub-millimeter range. The polymeric membrane can be utilized for capturing embolic particles within a lumen prior to, during or after a therapeutic intervention. The number, size and distribution of the pores within the membrane can generally be adjusted to effect a desirable degree of lumen blood permeability while maintaining an adequate filtering and/or retaining capability for embolic particles. Axial actuation of the wire scaffold during deployment can facilitate beneficial adaption to the underlying vascular anatomy with both controllable amount of radial force and dimensions, improving vessel anchoring capability and reducing risk of embolic particle migration. Upon reversal of the actuation, the wire scaffold can be collapsed, back-folding the membrane onto itself and allowing safe and efficient retrieval of the captured embolic particles.

The HATS catheter system can be designed to be guidable with a guide wire along the complete length of the instrument, so that the guide wire can enter at the distal catheter tip and exit at the proximal hub. For PTA catheters, such a design can be referred to as an over-the-wire ("OTW") configuration. Alternatively, the HATS catheter can contain a guide wire exit port positioned at a defined distance proximate to the hydraulic chamber, so that the guide wire is contained only within a limited, distally positioned guide wire lumen length or section. Such a design can be referred to as rapid exchange ("RX") configuration, and enables the instrument to be operated with a significantly shorter guide wire length. Additionally, the distal working end (i.e. the braided member or scaffold) can be provided in an on-the shaft or on-the wire configuration, which is further explained in the following two examples.

Thrombectomy Device

Figure 19:
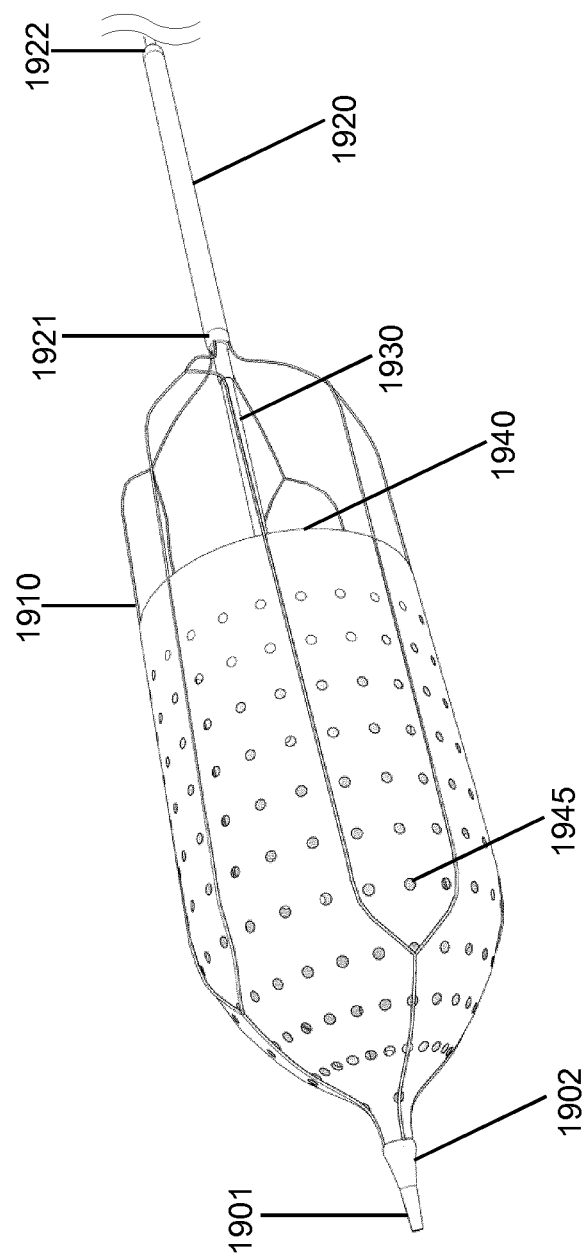
FIG. 19 provides an exemplary wire scaffold design in a deployed state and having an on-the shaft configuration, for facilitating thrombectomy, as an embodiment.

FIG. 19 provides an exemplary wire scaffold design in a deployed state and having an on-the shaft configuration, for facilitating thrombectomy, as an embodiment. In FIG. 19, the hydraulically actuatable wire scaffold 1910 located between a distal end plug 1902 and a proximal end plug 1921 is adhered to the hydraulic chamber casing 1920 and coaxially aligned over a distal catheter shaft portion having a catheter tip 1901. The wire scaffold further comprises a polymeric membrane 1940 interspersed with macroscopic pores 1945 in the sub-millimeter range. The polymeric membrane can be utilized for capturing a thrombotic mass and/or embolic particles within a lumen prior to, during or after a therapeutic intervention. The number, size and distribution of the pores within the membrane can generally be adjusted to effect a desirable degree of lumen blood permeability while maintaining an adequate filtering and/or retaining capability for blood clots and embolic particles. Axial actuation of the wire scaffold during deployment can facilitate beneficial adaption to the underlying vascular anatomy with both controllable amount of radial force and dimensions, improving vessel anchoring capability and reducing risk of embolic particle migration. By maintaining the braid member at a desired diameter, a radial gap between vessel and wire scaffold can be controllably generated to allow for the capturing of a thrombotic mass while avoiding traumatic vessel wall contact. Upon reversal of the actuation, the wire scaffold can be collapsed, back-folding the membrane onto itself and allowing safe and efficient retrieval of the captured thrombotic mass and/or embolic particles.

Figure 20:
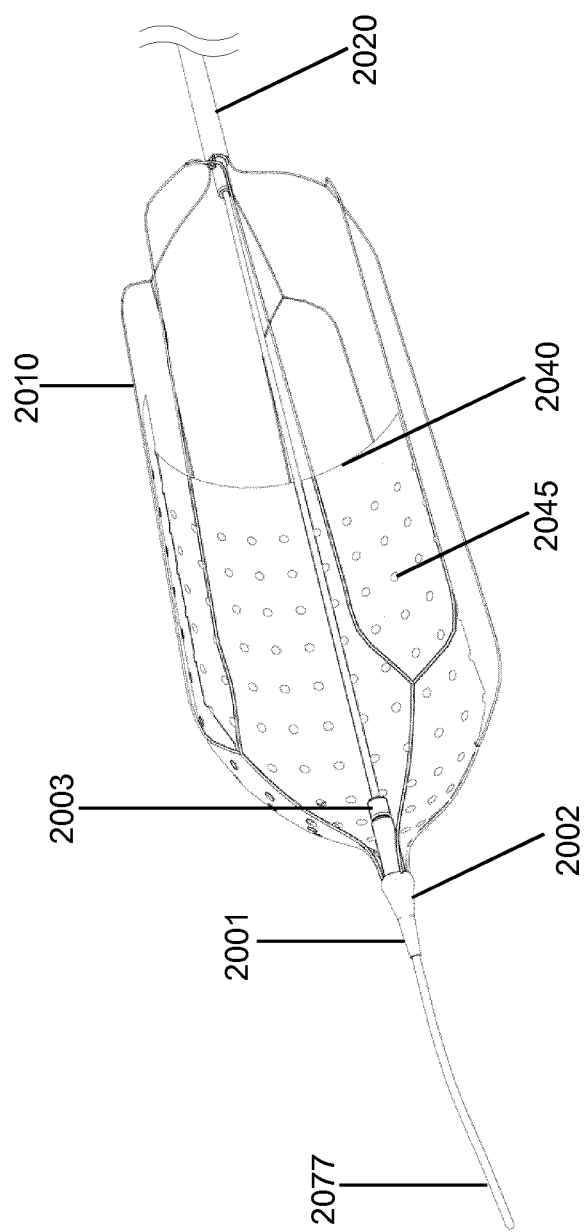
FIG. 20 illustrates a cross-sectional view of an exemplary wire scaffold design in a deployed state and having an on-the wire configuration, for facilitating thrombectomy, as an embodiment.

FIG. 20 illustrates a cross-sectional view of an exemplary wire scaffold design in a deployed state and having an on-the-wire configuration, for facilitating thrombectomy, as an embodiment. In FIG. 20, the hydraulically actuatable wire scaffold 2010 is positioned between a distal end plug 2002 converging into an atraumatic tip 2001, and a proximal end plug 2021 adhered to the hydraulic chamber casing 2020. The on-the wire configuration construction differs from the over-the-shaft configuration depicted in FIG. 19, in that the catheter shaft does not extend distally beyond the hydraulic chamber, and that the scaffold is instead coaxially aligned over an insertable guide wire 2077, having a distal end stop 2003. The end stop mechanically limits the distal propagation range of the proximal end plug adhered to a proximal portion of the wire scaffold. Further, additional fixation means such as a hemostatic seal (not shown), can be provided attached to the guide wire port of the manifold, to arrest the relative position between guide wire and catheter shaft. The wire scaffold further comprises a polymeric membrane 2040 interspersed with macroscopic pores 2045 in the sub-millimeter range. The polymeric membrane can be utilized for capturing a thrombotic mass and/or embolic particles within a lumen prior to, during or after a therapeutic intervention. The number, size and distribution of the pores within the membrane can generally be adjusted to effect a desirable degree of lumen blood permeability while maintaining an adequate filtering and/or retaining capability for blood clots and embolic particles. Axial actuation of the wire scaffold during deployment can facilitate beneficial adaption to the underlying vascular anatomy with both controllable amount of radial force and dimensions, improving vessel anchoring capability and reducing risk of embolic particle migration. Upon reversal of the actuation, the wire scaffold can be collapsed, back-folding the membrane onto itself and allowing safe and efficient retrieval of the captured thrombotic mass and/or embolic particles. The on-the wire configuration carries an added benefit over the on-the shaft configuration in that the wire scaffold, or interchangeably, a braided member can be delivered in extended state with a substantially decreased crossing profile.

Manufacture and Material Selection For Hats

The HATS catheter components can be manufactured from biocompatible, polymeric, metallic and ceramic materials. For example, the catheter components may be manufactured from aliphatic, semi-aromatic and aromatic polyamides and their respective blends, including PEBAX, GRILAMID and/or CRISTAMID; polyether ether ketones (PEEK); polyimides; linear and nonlinear, branched or non-branched, low molecular weight, medium molecular weight, or high molecular weight; low density, medium density, or high density polyolefins, including polyethylene (PE) and polypropylene (PP), silicones, thermoplastic elastomers, such as polyurethanes (TPEs), silicone and fluoro-elastomers, polycarbonates (PC), polyethylene terephthalate (PET) and combinations, including blends and copolymers of any of these materials.

The HATS catheter components can also be fabricated as a single layer, dual-layer, or multi-layer configurations. In the instance of dual-layer or multi-layer configurations, certain catheter elements, including for example the shaft may utilize the same material for each layer or may utilize different materials for each layer. The multiple layers can be glued, melted or fused together with an adhesive or employing a co-extrusion process. Alternatively, the multiple layers are not required to be attached or glued together, instead, the multiple layers may be allowed to move independently. Additionally, the durometer of the material(s) selected for each layer may be altered to further alter the performance aspects of the individual catheter components. Also, the chemical functionality and/or physical polarity of the material can be changed to enhance interfacial adhesion between the differing layers and/or to provide exposed surfaces and/or inner lumen with an increased lubriciousness or changed surface energy when in contact with a guide wire, injected liquids, or functional coatings, for example.

These chemical and physical treatments or alternations/variations may include for instance chemical additives that can introduce another chemical functionality to the interfacial surface, when added to an exemplary base polymer formulation intended to form one or more layers of the catheter component, for example, including functional groups such as carboxy- and/or amino groups, which can effectively enhance the underlying polarity of the layer and the substrate, thus facilitating enhanced adhesion and mechanical fixation strength in between one or more layered structures of catheter components.

Other surface modifications or plasma techniques can be employed for changing the chemical and/or the mechanical properties of the underlying substrate, wherein the plasma modification of the material(s) may affect the polarity and/or the surface energy of the balloon layer(s). Other suitable techniques may incorporate additives, adhesives and/or filling agents, which can introduce other beneficial properties to catheter materials. For example, catheter shaft, tip, hydraulic chamber and/or braided member may incorporate radiopaque elements that can be provided embedded within polymeric materials to selectively increase fluoroscopic visibility at desired component locations. Additionally the shaft and/or the hydraulic chamber components may incorporate fluoropolymer-based filler particles/fibers to permanently decrease the frictional coefficient as compared to an untreated base-polymer formulation or activatable, single-use coatings. Furthermore, the shaft, hydraulic chamber and/or braided member can be reinforced and may contain metal or polymer-based strands, fibers, wires, braids, meshes and/or fabrics embedded as layers, sections or regions into the base material.

The HATS catheter components can be manufactured by following various methods known to persons skilled in the art, including: single-, dual-, and or multilayer extrusion, blow molding, dip molding, deposition or other manufacturing methods suitable for manufacturing HATS catheter components. The material for forming HATS catheters may be subjected to mechanical processes before, during or after the catheter manufacture. If an extrusion process is utilized for the manufacturing process, the tubular member for forming the shaft member can be stretched before or during the extrusion process. The temperature, the extrusion pressure, or other parameters can be changed during the manufacturing processes to affect the properties of the manufactured shaft.

The foregoing description, for purposes of explanation, refers to specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and practical applications, to thereby enable others skilled in the art to best utilize the invention and various embodiments with various modifications as suitable for the particular uses contemplated. It is intended that the scope of the invention be defined by the following claims and their equivalent.

We claim:

1. A catheter system (100), comprising:
    a catheter shaft (130) including a distal catheter tip portion (131);
    a hydraulic chamber (120) capable of a transitional displacement along a longitudinal axis of the catheter shaft (130); and
    a braided member (110) located between the catheter tip portion (131) and the hydraulic chamber (120) and being extensible along the longitudinal axis of the catheter shaft (130);
    wherein the transitional displacement of the hydraulic chamber (120) exerts force on the braided member (110) such that it controllably facilitates the axial actuation of the braided member (110) effecting a variable adjustable radial force;
    characterized in that the hydraulic chamber (120) comprises:
    an outer tubular member (219) having a distal end plug (211) and a proximal end plug (220); and
    an elongate inner tubular member that forms the catheter shaft (216);
    wherein the hydraulic chamber (120) is formed by a proximal lateral surface of an annular distal seal (212), a distal lateral surface of an annular proximal seal (214), an internal surface of the outer tubular member and an external surface of the inner tubular member,
    wherein the annular distal seal is formed from the internal surface of the outer tubular member, the annular proximal seal is formed from the external surface of the inner tubular member; and
    a hydraulic fluid port (213) is formed as a lateral opening in a surface of the catheter shaft, positioned between the proximal and distal seal and maintaining the hydraulic chamber in fluid-tight communication with a hydraulic lumen in the catheter shaft.

2. The catheter system according to claim 1, wherein the braided member (110) is bi-directionally extensible along the longitudinal axis of the catheter shaft (130).

3. The catheter system according to claim 1, further comprising an extension member that extends the outer tubular shaft distally between the hydraulic chamber (120) and the braided member (110), wherein the transitional displacement of the hydraulic chamber (120) exerts force on the braided member (110) via the extension member.

4. The catheter system according to claim 1, wherein the distal end portion of the braided member (110) is affixed to the catheter tip portion (131) and/or a proximal end portion of the braided member (110) is affixed to the distal end portion of the hydraulic chamber (120) or the distal end portion of an extension member.

5. The catheter system according to claim 1, wherein the catheter shaft (130) comprises:
    a distal end stop (215) positioned proximal to the distal seal inside the hydraulic chamber; and
    a proximal end stop (221) positioned proximal to the distal end plug outside the hydraulic chamber, wherein both end stops are extending from the catheter shaft surface, futher wherein the relative positions of both end stop to each other define a maximum actuation distance of the hydraulic chamber.

6. The catheter system according to claim 1, wherein the braided member (110) is formed from radiopaque shape memory alloy, spring-metal, or rigid polymer based wire filaments wound at a predetermined braiding angle into a helical braided mesh of counter-rotating wire pairs heat-set into a nominal shape.

7. The catheter system according to claim 6, wherein the nominal shape defines a cylindrical form having at least a first and a second taper about a length axis.

8. The catheter system according to claim 6, wherein the nominal shape defines a cylindrical form having two or more different diameters along a length axis.

9. The catheter system according to claim 6, wherein the nominal shape defines a cylindrical form having a continuously varying diameter along a length axis.

10. The catheter system according to claim 6, wherein the braiding angle is kept the same or different across one or more diameter variations of the braided member.

11. The catheter system according to claim 6, wherein the mesh size of the braided member is kept the same or different across one or more length portions of the braided member.

12. The catheter system according to claim 6, wherein the nominal shape of the braided member is hydraulically actuatable between extended and compressed states, effecting a desired dimensional change of a) length, b) diameter, c) mesh size, d) permeability, e) radial force, f) flow diversion and g) foreign body entrapment capability of the braided member.

13. The catheter system according to claim 1, wherein at least one portion of the braided member (110) is covered with a porous polymeric liner.

14. The catheter system according to claim 1, wherein the proximal and distal seal are formed from a thermoplastic elastomer.

15. The catheter system according to claim 1, wherein the proximal and distal seal are provided structurally reinforced by distal (223) and proximal annular lateral constraint members (224).

16. The catheter system according to claim 1, wherein the distal seal is positioned stationary with respect to the outer tubular member (219), and wherein the proximal seal is positioned stationary with respect to the inner member (216).

* * * * *